US010081690B2

(12) United States Patent
Huang et al.

(10) Patent No.: US 10,081,690 B2
(45) Date of Patent: Sep. 25, 2018

(54) POWDERY DIACETAL CLARIFYING AGENT AND METHOD OF PREPARING THE SAME

(71) Applicant: Sunko Ink Co., Ltd., Taichung (TW)

(72) Inventors: Ting-Ti Huang, Taichung (TW); Chiu-Peng Tsou, Taichung (TW); Tien-Chu Chang, Taichung (TW); Ming-Chang Hsieh, Taichung (TW); Chen-Ku Hsieh, Taichung (TW)

( * ) Notice: Subject to any disclaimer, the term of this patent is extended or adjusted under 35 U.S.C. 154(b) by 37 days.

(21) Appl. No.: 15/190,302

(22) Filed: Jun. 23, 2016

(65) Prior Publication Data

US 2017/0369611 A1   Dec. 28, 2017

(51) Int. Cl.
*C08F 210/06* (2006.01)
*C08F 210/16* (2006.01)

(52) U.S. Cl.
CPC ......... *C08F 210/16* (2013.01); *C08F 210/06* (2013.01)

(58) Field of Classification Search
None
See application file for complete search history.

(56) References Cited

U.S. PATENT DOCUMENTS

| | | | |
|---|---|---|---|
| 4,429,140 A | 1/1984 | Murai et al. | |
| 5,023,354 A | 6/1991 | Salome et al. | |
| 5,731,474 A | 3/1998 | Scrivens et al. | |
| 6,355,772 B1* | 3/2002 | Gruber | A61L 15/26 264/165 |
| 6,899,939 B2* | 5/2005 | Haese | C08K 5/103 428/64.7 |
| 2007/0060697 A1* | 3/2007 | Li | C08K 5/1575 524/493 |
| 2009/0111918 A1* | 4/2009 | Tsou | C08K 5/1575 524/108 |
| 2011/0136959 A1* | 6/2011 | Brandstetter | C08L 23/10 524/451 |
| 2016/0264755 A1* | 9/2016 | Lee | C10M 159/18 |

FOREIGN PATENT DOCUMENTS

| | | |
|---|---|---|
| CN | 103391966 | 11/2013 |
| EP | 1505109 | 2/2005 |
| TW | 200407376 | 5/2004 |
| TW | 201439095 | 10/2014 |
| TW | 201540762 | 11/2015 |

* cited by examiner

*Primary Examiner* — Joseph D Anthony

(57) ABSTRACT

Provided are a powdery diacetal clarifying agent and a method of preparing the same. The powdery diacetal clarifying agent comprises a diacetal compound and an inorganic silicon-containing compound having a pH value equal to or more than 6 and equal to or less than 12. The powdery diacetal clarifying agent of the composition can have excellent flowability, dispersability, thermal resistance, and color stability. Accordingly, the powdery diacetal clarifying agent does not release stinking odor and incur yellowing at high temperature, allowing the plastic articles to have improved appearance and visual appeal.

8 Claims, 7 Drawing Sheets

POWDERY DIACETAL CLARIFYING AGENT AND METHOD OF PREPARING THE SAME

BACKGROUND OF THE INVENTION

1. Field of the Invention

The present invention relates to a powdery clarifying agent for plastics such as polyolefin, more particularly to a powdery diacetal clarifying agent comprising specific di(arylidene)-D-sorbitol. The present invention also relates to a method of preparing the powdery diacetal clarifying agent.

2. Description of the Prior Arts

Transparent plastic articles made of polyolefins enable visibility of contents thereof, and thus have been widely used in various industries. Di(arylidene)-D-sorbitol acting as a nucleating agent for polyolefins is useful to shorten the molding period and improve the physical properties of the polyolefin articles. Moreover, di(arylidene)-D-sorbitol can be used as a clarifying agent to increase the transparency of semi-crystalline polyolefin articles.

A commonly accepted understanding on the mechanism of a di(arylidene)-D-sorbitol-initiated clarification process is as follows. Diacetal powders, e.g., di(arylidene)-D-sorbitol powders, added to polyolefins and melted at a proper temperature afterwards, crystallize and disperse in the cooling and molding process of the polyolefin plastic. The crystallized and dispersed diacetal powders develop a crystallizing network. In the crystallizing network, a multitude of spherical nucleation sites are formed. The nucleation sites are of a size too small to initiate scattering of visible light, thereby allowing the polyolefin article to be transparent. Accordingly, the transparent plastic articles are widely used in household utensils, large-scale storage boxes, electronic appliances, medical apparatuses, automobile anti-freezing, and food packaging products.

Di(arylidene)-D-sorbitol derivatives, for example, 1,3:2,4-di(4-methyl-benzylidene)-D-sorbitol (MDBS), 1,3:2,4-di(4-chloro-benzylidene)-D-sorbitol (CDBS), 1,3:2,4-di(4-ethyl-benzylidene)-D-sorbitol (EDBS), 1,3:2,4-di(3,4-dimethyl-benzylidene)-D-sorbitol (DMDBS), and di(methyl-thenylidene)-D-sorbitol (MDTS) are commonly disclosed in patent publications and developed as commercial compounds. As the customers are concerned more about the safety, transparency, appearance, and quality of the plastic articles, how to develop a plastic article with the foresaid marketing demands has been a crucial issue in the related fields. However, the conventional powdery diacetal clarifying agent has at least the following problems to be solved.

Firstly, insufficient dispersion resulted from miniaturization of conventional powdery diacetal clarifying agent and aggregation under heavy storage load are awaited to be solved.

When the particle size of the conventional powdery diacetal clarifying agent added to polyolefin are too large to be well dispersed, the polyolefin products often show visible white spots and are identified as defective products. In order to miniaturize the conventional powdery diacetal clarifying agent, extra energy is consumed during the grinding treatment, which reduces the production yield and raises the production cost.

Even if the insufficient dispersion or aggregation could be overcome, the conventional powdery diacetal clarifying agent of small size is apt to aggregate, have larger friction, and be adhered by water at larger proportion of the surface area. As a result, other problems of reduction in flowability and undesired adherence on the inner wall of the equipment are incurred in the process of the conventional powdery diacetal clarifying agent.

More seriously, the static electricity produced during grinding treatment not only causes the conventional powdery diacetal clarifying agent to be suspended more intensively, but also contributes to a more severe aggregation among these powders. As a result, the polyolefin articles are still produced with visible white spots and identified as defective products as before.

For example, Taiwan Patent Application Publication No. 201439095 (Sukehiro et al., New Japan Chemical Co., Ltd.) discloses a powdery diacetal-containing composition, which comprises component (A): a specific diacetal, component (B): a polyoxyethylene sorbitan C8-C22 fatty acid ester, and component (C): a specific fatty acid metal salt. Sukehiro et al. uses an antistatic agent and a slip agent to prevent the diacetal powders from being caked during the storage and tries to avoid the adherence or cross-linking of diacetal powders in the tube, the supply box, or the feeder. Unfortunately, the remaining slip agent and antistatic agent are suspected to deteriorate the thermal resistance under high temperature and the safety of the food package, which cannot be directly used in various fields.

U.S. Patent Application Publication No. 2009/0111918 (Tsou et al., Kuo Ching Chemical Co., Ltd.) discloses a method of preparing the diacetal clarifying agent. A crude produce obtained from a reaction of aromatic aldehyde and polyol in the presence of acid catalyst is added with organosilane treated fume silica having a pH value of 5.5 to 8 to control their granular size, and thus prepare a superfine powdery diacetal composition. Accordingly, said powdery diacetal composition of high dispersability does not cause the visible white spots in the plastic articles. Nevertheless, a specific machine is required to inhibit the powdery diacetal composition suspended in air during the process.

Secondly, flowability of the conventional diacetal clarifying agent powders is awaited to be improved for easy operation.

To increase the flowability, a conventional method in the prior art mixes a flow agent such as fume silica having a pH less than 4 at its surface, calcium stearate with a little remaining fatty acid, and a slip agent with the powdery diacetal clarifying agent. When the powdery diacetal clarifying composition is employed under high temperature, a trace of remaining acid will facilitate the aging and yellowing of the plastics, and thus degrades the appearance of the final articles.

For example, U.S. Patent Application Publication No. 2007/0060697 (Li et al.) discloses blending a commercial powdery diacetal clarifying agent and a fume silica for improving the flowability. However, a specific equipment is still needed to inhibit the powdery diacetal composition suspended in air.

Thirdly, thermal resistance of the conventional powdery diacetal clarifying agent is awaited to be improved in order to inhibit the occurrences of yellowing during plastics processing, the release of stinking odor, and color shift of the final articles.

U.S. Pat. No. 4,429,140 (Murai et al.) discloses a method of preparing a dibenzylidene sorbitol (DBS) clarifying agent by reacting sorbitol with benzaldehyde or alkyl acetal derivative in the presence of an acid catalyst, a hydrophobic organic solvent, and a water-soluble organic polar solvent.

However, the conventional process for DBS releases stinking odor during plastic processing.

U.S. Pat. No. 5,023,354 (Murai et al.) discloses another method of preparing diacetals. The benzoic aldehyde reacts with polyol having five or more hydroxyl groups and an arylsulfonic acid in an aqueous solution, then the condensation product is neutralized, filtered, and washed to obtain a 1,3:2,4-di(substituted benzylidene) sorbitol of a purity more than 95%. Another method of preparing acetals disclosed in U.S. Pat. No. 5,731,474 (Scrivens et al., Milliken Research Corporation) employs a benzoic aldehyde, a polyol having five or more hydroxyl groups, an acid catalyst, a hydrophobic organic solution, and an additive selected from the group consisting of dihydric alcohol, trihydric alcohol, and tetrahydric alcohol to undergo a condensation under heating, and then purified to obtain 1,3:2,4-di(substituted benzylidene) sorbitol. Although the acetals prepared by Scrivens et al. have a purity up to 97%, neither Murai et al. nor Scrivens et al. mentions the techniques to inhibit the stinking odor and yellowing under high temperature.

Taiwan Patent Application Publication No. 200407376, Taiwan Patent No. 1318994 and European Patent No. 1505109 (Masahide et al., New Japan Chemical Co., Ltd.) uses a diacetal composition comprising diacetal and long-chain aliphatic alcohol or carboxylic acid having hydroxyl group as a nucleating agent to reduce the temperature for dissolving diacetals, inhibit the dissipation of alcohols, or suppress the migration of odor components. Further, Masahide et al. also discloses an inhibitor comprising diacetal, C6-C32 saturated or unsaturated aliphatic alcohol and an anionic surfactant or at least one aliphatic amine to decrease the process temperature and suppress the odor. However, high temperature is often needed to obtain the desired transparency or shaping, and the insufficient thermal resistance often shifts the color of the plastic articles. Moreover, the disclosed inhibitor with high lipophilicity raises concerns about being migrated by greasy food.

Taiwan Patent Application Publication No. 201540762 (Tsou et al., Kuo Ching Chemical Co., Ltd.) discloses a method of preparing a diacetal clarifying agent, which employs a hydrogenating agent to remove the odor-releasing impurities, thereby increasing the purity of the diacetal clarifying agent.

Nevertheless, the aforementioned disclosures are silent on how to prevent the diacetal from being partially decomposed by the remaining acid when the diacetal clarifying agent is employed with antioxidant, flow agent, filler, pigment, or slip agent. Thus, the problems of yellowing or lack of transparency still exist in the prior art.

In the processing of plastic articles, it is common to blend a fluorescent whitening agent or a pigment into the plastic composition. China Patent Application Pub. No 103391966 adds the pigment into the conventional powdery sorbitol diacetal clarifying agent to change the visual perceptions. But, the influences on visual perceptions depend on the mixing ratio and the mixing uniformity, and the safety of the fluorescent whitening agent and the pigment also limits the uses of the plastic articles.

As a result, there is a need to overcome or mitigate the negative influences on the conventional diacetal clarifying agent. Upon maintaining the safety of the diacetal clarifying agent, how to improve the overall performance of the transparent plastic articles becomes an important issue in the plastic industry.

SUMMARY OF THE INVENTION

The objective of the present invention is to improve the powdery diacetal clarifying agent and enable the plastic articles made from the powdery diacetal clarifying agent to provide the following technical effects:

1. low yellow index, easy operation, and good thermal resistance;

2. no stinking odor released during the plastic processing;

3. good tolerance to high temperature when mixing the plastic raw materials;

4. good color stability to the final plastic articles made from the powdery diacetal clarifying agent;

5. improved transparent appearance and visual appeal of the final plastic articles made from the powdery diacetal clarifying agent.

To achieve the foresaid objective and technical effects, the present invention provides a powdery diacetal clarifying agent suitable for polyolefins. The powdery diacetal clarifying agent comprises component (A): a specific diacetal compound and component (B): an inorganic silicon-containing compound having a pH value of 6 to 12.

The powdery diacetal clarifying agent in accordance with the present invention can provide good flowability and good dispersability to avoid being suspended or caked after storage, and thus is easy for transport operation. In addition, the powdery diacetal clarifying agent also has a good dispersion to avoid aggregation when added with the polyolefin material. Accordingly, the powdery diacetal clarifying agent improves the uniformity in transparency or nucleation of the polyolefin articles; and more especially, provides a good tolerance to high temperature during the process, does not release stinking odor, and has a good color stability during the process.

Preferably, the powdery diacetal clarifying agent in accordance with the present invention is directed to a specific diacetal compound and an inorganic silicon-containing compound uniformly dispersed therein. Preferably, the powdery diacetal clarifying agent comprises more than 96.5 wt % of the diacetal compound and 0.02 wt % to 3.5 wt % of the inorganic silicon-containing compound. More preferably, the powdery diacetal clarifying agent comprises more than 98.5 wt % of the diacetal compound and 0.02 wt % to 1.5 wt % of the inorganic silicon-containing compound. Even more preferably, the powdery diacetal clarifying agent comprises more than 99 wt % of the diacetal compound and 0.02 wt % to 1 wt % of the inorganic silicon-containing compound.

In accordance with the present invention, the diacetal compound is selected from the group consisting of compounds represented by formulae (I) to (V):

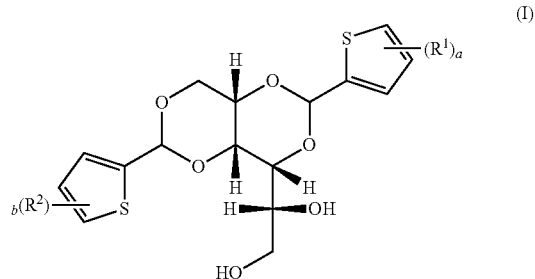

-continued

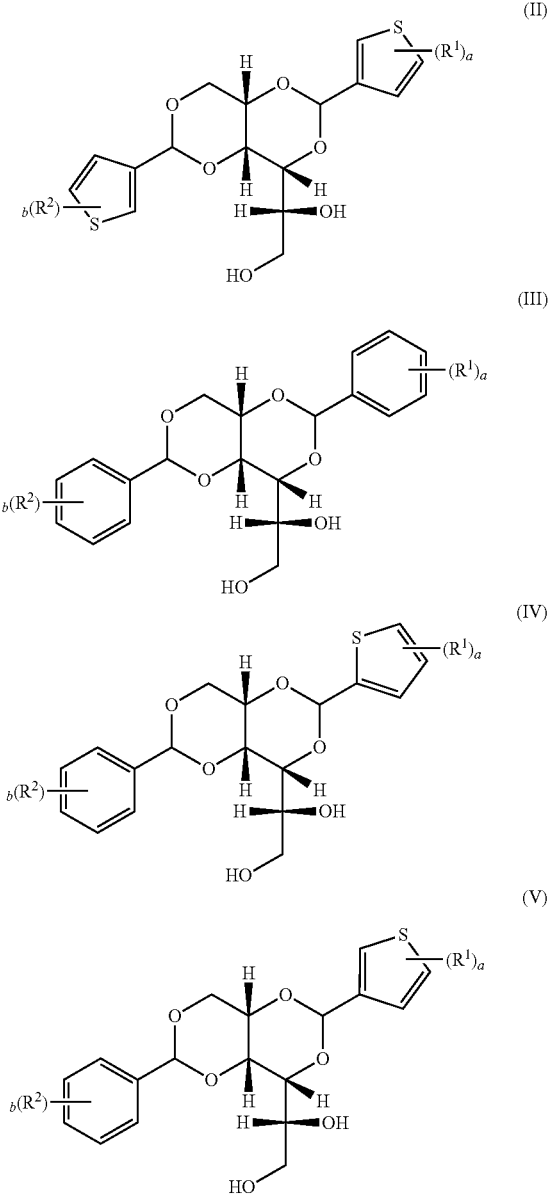

wherein R¹ and R² may be each independently hydrogen, an alkyl group having 1 to 4 carbon atoms, an alkoxy group having 1 to 4 carbon atoms, an alkoxycarbonyl group having 1 to 4 carbon atoms, fluoro, chloro, and bromo; and a and b are each independently an integral from 0 to 3.

For example, the diacetal compound may be, but is not limited to, 1,3:2,4-di(5-methyl-2-thenylidene)-D-sorbitol; 1,3:2,4-di(4-methyl-benzylidene)-D-sorbitol; 1,3:2,4-di(4-n-butyl-benzylidene)-D-sorbitol, and 1,3:2,4-di(3,4-dimethyl-benzylidene)-D-sorbitol The inorganic silicon-containing compound in accordance with the present invention is directed to inorganic silicon-containing fine powders which can be well dispersed in an organic polar solvent or an aqueous suspension. Said inorganic silicon-containing compound has a median particle size less than 15 micrometers and has a pH value from pH 6 to pH 12.

Preferably, the pH value of the inorganic silicon-containing compound is equal to or more than 8 and equal to or less than 10, and the median particle size of the inorganic silicon-containing compound is equal to or less than 10 micrometers.

For example, in a first embodiment, the inorganic silicon-containing compound is an exfoliated montmorillonite silica nanomaterial with a median particle size less than 1 micrometer, and the pH value of the exfoliated montmorillonite silica nanomaterial is from pH 9 to pH 10. In a second embodiment, the inorganic silicon-containing compound is a lithium magnesium sodium oxide silicate with a median particle size less than 50 nanometers, and the pH value of the lithium magnesium sodium oxide silicate is from pH 9 to pH 10. In a third embodiment, the inorganic silicon-containing compound is a sodium aluminosilicate containing trisulfur radical anion ($S_3^-$).

Preferably, an amount of the inorganic silicon-containing compound ranges from 0.02 wt % to 3.0 wt % based on a total amount of the powdery diacetal clarifying agent. More preferably, the amount of the inorganic silicon-containing compound ranges from 0.02 wt % to 1.0 wt % based on the total amount of the powdery diacetal clarifying agent.

The present invention also provides a method of preparing the powdery diacetal clarifying agent, which comprises the following steps: (1) reacting an aromatic aldehyde with sorbitol in the presence of an organic acid catalyst in an alcohol solvent to obtain a diacetal mixture; (2) adding an inorganic hydrogenating agent to remove the impurity in the diacetal mixture; (3) adding an inorganic silicon-containing agent having a pH value of pH 6 to pH 12; and (4) filtering the mixture to remove the impurity and drying the mixture to obtain the powdery diacetal clarifying agent.

The powdery diacetal clarifying agent modified by the inorganic silicon-containing agent can have good flowablity and overcome the problems of powder suspended in air and aggregation. More particularly, the powdery diacetal clarifying agent has an excellent thermal stability and superior appearance and color stability compared with those of the conventional diacetal products.

In addition, the powdery diacetal clarifying agent in accordance with the present invention does not release intolerable or stinking odor when mixed at 220° C. to 230° C. or injected at the die, and the plastic plaque made therefrom does not show the visible white spots. More preferably, the powdery diacetal clarifying agent has a color stability superior to commercial products; and more particularly, it is useful to improve the appearance and visual appeal of the plastic article.

In accordance with the present invention, a method of preparing the powdery diacetal clarifying agent comprises the steps of:

(a) mixing an aromatic aldehyde, a polyol, and an acid catalyst in an organic polar solvent to obtain a first reaction mixture, wherein an equivalence ratio of the aromatic aldehyde to the polyol is from 2:1 to 2:2;

(b) adding a hydrogenating agent and an inorganic silicon-containing agent into the first reaction mixture to obtain a second reaction mixture, wherein an equivalence ratio of the hydrogenating agent to the aromatic aldehyde is more than 0.01:1, a pH value of the inorganic silicon-containing agent is from pH 6 to pH 12, and an amount of the inorganic silicon-containing agent ranges from 0.02 wt % to 3.5 wt % based on an amount of the aromatic aldehyde;

(c) filtering and drying the filtered second reaction mixture to obtain the powdery diacetal clarifying agent.

More specifically, the method comprises the steps of:

(a) mixing an aromatic aldehyde, a polyol, and an acid catalyst in an organic polar solvent to obtain a first reaction mixture, wherein an equivalence ratio of the aromatic aldehyde to the polyol is from 2:1 to 2:2;

(b1) adding a hydrogenating agent into the first reaction mixture to obtain a precipitate, wherein an equivalence ratio of the hydrogenating agent to the aromatic aldehyde is more than 0.01:1;

(b2) adding an inorganic silicon-containing agent into the precipitate to obtain a second reaction mixture, wherein a pH value of the inorganic silicon-containing agent is from pH 6 to pH 12, and an amount of the inorganic silicon-containing agent ranges from 0.02 wt % to 3.0 wt % based on an amount of the aromatic aldehyde;

(c) filtering the second reaction mixture to obtain a filtered second reaction mixture, drying the filtered second reaction mixture to obtain a solid mixture, and grinding the solid mixture to obtain the powdery diacetal clarifying agent.

After the grinding step, the particle size distribution of the prepared powdery diacetal clarifying agent can meet the requirement of commercial product, i.e., D97 less than 45 micrometers. More preferably, the prepared powdery diacetal clarifying agent can have D97 less than 30 micrometers to disperse in polyolefin well and uniformly, thereby improving the transparency of the plastic article.

Examples of the inorganic silicon-containing agent include, but are not limited to, the following nine specific agents.

1. CAS No. 12736-96-8 may be Minbloc® HC-400 (from Unimin, New Canaan, Conn.), pH 9.9. It is sodium potassium aluminosilicate of 2.8 μm median particle size.

2. CAS No. 13983-17-0 or CAS No. 7699-41-4 may be Wollastonite Nyad® 5000 obtained from Nyco Minerals, Calgary, Alberta, Canada), i.e., Wollastonite, pH 9.9 (10% aqueous suspension). It is calcium silicate of 2.2 μm median particle size. Chemical formula: $Ca(SiO_3)$.

3. CAS No. 1327-39-5 may be Silton® JC30 (from Mizusawa Chemical, Tokyo, Japan), pH 7 to pH 9. It is sodium calcium aluminosilicate of 3 μm median particle size.

4. CAS No. 1344-00-9 may be Tixolex® 17 (from Solvay), pH 9.5 to pH 10.5 (5% aqueous suspension); or Sipernat® 44MS (from Evonik, formerly Degussa, Essen, Germany), pH 11.5 (10% aqueous suspension). Tixolex® 17 is sodium aluminosilicate of 5 μm to 7 μm median particle size. Sipernat® 44MS is sodium aluminosilicate of 3.5 μm median particle size.

5. CAS No. 12001-26-2 may be Suzorite mica 400-HK (from Kings Mountain Minerals/Zemex Industrial Minerals, Atlanta, Ga.), i.e., a mica, pH 9.2. It is potassium magnesium aluminosilicate of 15 μm median particle size.

6. CAS No. 57455-37-5 may be Ultramarine Blue, also called C.I. Pigment Blue 29 (pH 6 to pH 9); or Ultramarin Blue N-1200, Ultramarin Blue No. 2000, Ultramarin Blue N-2041, Ultramarin Blue N-2350, or Ultramarin Blue N-3152, (pH 8.5 to pH 10.5, obtained from Daichi Kaei Kogo Co., Ltd. Japan). It is a natural or synthetic inorganic pigment, i.e., sodium aluminosilicate containing trisulfur radical anion ($S_3^-$).

7. CAS No. 1344-01-0 may be Silton® JC50 (from Mizusawa Chemical, Tokyo, Japan), pH 7 to pH 9. It is sodium calcium aluminosilicate of 5 μm median particle size.

8. CAS No. 1318-93-0 may be Cloisite® Na$^+$ (from Southern Clay Products, Gonzales, Tex.), pH 9.0 (2% aqueous suspension); or NSP103 (nano silicate plate, from JJ Nano Technology Co., Ltd.), pH 9 to pH 10 (1 wt % aqueous suspension). Cloisite® Na$^+$ is a modified montmorillonite or hydrated aluminosilicate, whose chemical formula is represented by $(Al_{1.33-1.67}Mg_{0.33-0.67})(Ca_{0-1}Na_{0-1})_{0.33}Si_4(OH)_2 O_{10}\cdot x\ H_2O$. Besides, NSP103 is an aqueous suspension of exfoliated montmorillonite silica nanomaterial with a median particle size less than 1 micrometer (See Taiwan Patent No. I270529).

9. CAS No. 227605-22-3 may be Laponite® RD (Southern Clay Products), pH 9 to pH 10 (2% aqueous suspension). It is synthetic layered lithium magnesium sodium oxide silicate with a chemical formula of $Li_{0.03}Mg_{0.39}Na_{0.07}O_{0.15} (Si_2O_5)_{0.28}$, and has a median particle size less than 50 nm.

Preferably, the inorganic silicon-containing agent may be at least one inorganic silicon-containing fine powder or aqueous suspension containing the inorganic silicon-containing compound, which has a pH value from pH 8 to pH 10 and a median particle size less than 10 micrometers.

In accordance with the present invention, the equivalence ratio of the aromatic aldehyde to the polyol is preferably from 2:1.05 to 2:1.3. The equivalence ratio of the hydrogenating agent to the aromatic aldehyde is preferably from 0.03:1 to 0.3:1.

Preferably, the amount of the inorganic silicon-containing agent ranges from 0.2 wt % to 1.0 wt % based on the amount of the aromatic aldehyde.

Preferably, the aromatic aldehyde applicable to the present invention may be a thiophenecarboxaldehyde based compound, a benzaldehyde based compound, or their combination. The thiophenecarboxaldehyde based compound may be unsubstituted thiophenecarboxaldehyde or substituted thiophenecarboxaldehyde having 1 to 3 substitution group(s). The substitution group(s) is selected from the group consisting of: an alkyl group having 1 to 4 carbon atoms, an alkoxy group having 1 to 4 carbon atoms, an alkoxycarbonyl group having 1 to 4 carbon atoms, and halo, e.g., fluoro, chloro, and bromo. For example, the thiophenecarboxaldehyde based compound may be 5-methyl-2-thiophenecarboxaldehyde. The benzaldehyde based compound may be unsubstituted benzaldehyde or substituted benzaldehyde having 1 to 3 substitution group(s). As stated above, the substitution group(s) is selected from the group consisting of: an alkyl group having 1 to 4 carbon atoms, an alkoxy group having 1 to 4 carbon atoms, an alkoxycarbonyl group having 1 to 4 carbon atoms, and halo, e.g., fluoro, chloro, and bromo. For example, the benzaldehyde may be, but is not limited to, 4-methyl benzaldehyde, 4-n-butyl benzaldehyde, or 3,4-dimethyl benzaldehyde.

Preferably, the acid catalyst applicable to the present invention may be sulfuric acid, phosphoric acid, hydrochloric acid, methanesulfonic acid, camphor sulfonic acid, p-toluene sulfonic acid, naphthalene sulfonic acid, or any combination thereof.

Preferably, the organic polar solvent applicable to the present invention may be, but is not limited to, methanol, ethanol, dimethyl formamide, acetonitrile, water or any combination thereof. In accordance with the present invention, the solution used for mixing with the precipitated product may be, but is not limited to, methanol. In accordance with the present invention, the undesired reactants, intermediates and impurities can be dissolved in the solution and the desired diacetals can be precipitated under a mild condition. The highly pure final products, i.e., powdery diacetal clarifying agent, can be easily removed from the reactants, intermediates and impurities through safe filtering and washing steps. Thus, the method of preparing the powdery diacetal clarifying agent is much simpler and safer than the conventional method.

Preferably, the hydrogenating agent applicable to the present invention may be sodium hydride (NaH), potassium hydride (KH), aluminium hydride (AlH), sodium cyanoborohydride (NaBH$_3$(CN)), diisobutylaluminium hydride (((i-C$_4$H$_9$)$_2$AlH)$_2$), lithium borohydride (LiBH$_4$), sodium borohydride (NaBH$_4$), potassium borohydride (KBH$_4$), calcium borohydride (Ca(BH$_4$)$_2$) or any combination thereof. More preferably, the hydrogenating agent may be sodium borohydride or potassium borohydride (KH).

More preferably, the hydrogenating agent is sodium borohydride or potassium borohydride. Accordingly, the hydrogenating agent can be employed to react with the aromatic aldehyde to assure the process safety of powdery diacetal clarifying agent.

Here, said hydrogenating agent may be made in powder, tablet or liquid form to mix with the first reaction mixture. Commercially available hydrogenating agent comprises, but is not limited to: VenPure™ AF (highly pure sodium borohydride tablets), VenPure™ SF (highly pure sodium borohydride powders), VenPure™ solution (a solution including sodium hydroxide and sodium borohydride, whose concentration is adjustable) or VenPure™ K (highly pure potassium borohydride powders).

Accordingly, the method of preparing the powdery diacetal clarifying agent can make the undesired substances remaining in the first reaction mixture, which releases stinking odor and has low thermal stability, be reacted into low odor and easily-purified substances by reacting an appropriate hydrogenating agent with the first reaction mixture. In addition, by means of mixing the precipitate with a specific inorganic silicon-containing agent, the powdery diacetal clarifying agent, substantially free of impurities, releasing no stinking odor, and having high thermal resistance, can be easily prepared through the filtration and drying steps.

Preferably, the method in accordance with the present invention is useful to prepare a highly pure powdery diacetal clarifying agent, which has a purity more than 98.5% determined by HPLC and contains less than 50 ppm of the aromatic aldehyde (impurity). Here, the purity of the powdery diacetal clarifying agent is determined by high performance liquid chromatography (HPLC), and the residue of the aromatic aldehyde is determined by gas chromatography (GC). More preferably, the prepared powdery diacetal clarifying agent has a HPLC purify more than 99% and cannot be detected to contain any aromatic aldehyde.

The present invention also provides a plastic composition with low yellow index, which comprises the foresaid powdery diacetal clarifying agent with good thermal resistance and polyolefin material.

Preferably, an amount of the highly pure powdery diacetal clarifying agent ranges from 0.05 wt % to 0.5 wt % based on the total amount of the plastic composition. More preferably, the amount of the highly pure powdery diacetal clarifying agent ranges from 0.1 wt % to 0.3 wt % based on the total amount of the plastic composition.

The polyolefin material applicable to the present invention has a crystallinity of 5% to 100%. Preferably, the polyolefin material is a crystalline resin having a crystallinity of 15% to 95%, such as polyethylene based resin, polypropylene based resin and polybutylene based resin. The catalyst used for preparing the polymer is not particularly limited. Conventional catalysts, such as radical polymerization catalyst, Ziegler-Natta catalyst, magnesium halide supported transition metal catalyst, metallocene catalyst, and catalyst combined with alkylaluminum compound, e.g., triethyl aluminum or chlorodiethylalumane, are available.

The polyethylene based resin may be high-density polyethylene, medium-density polyethylene, low-density polyethylene, linear low-density polyethylene or ethylene copolymer containing 50 wt % or more of ethylene. The polypropylene based resin may be polypropylene homopolymer or propylene copolymer containing 50 wt % or more of propylene. The polybutylene based resin may be polybutylene homopolymer or butylene copolymer containing 50 wt % or more of butylene. The foresaid copolymer may be random copolymer or block copolymer, and the stereoregularity of resin may be cis-form or trans-form.

The monomers of the copolymer may be α-olefin such as ethene, propene, butene, pentene, hexene, heptene, octane, nonene, decene, undecene, dodecene; dicyclo monomer such as 1,4-bicyclo[2.2.1]hepta-2,5-diene; methyl acrylate based monomer such as methyl methacrylate and methyl ethyl acrylate; ethyl acetate; maleic acids are available.

The powdery diacetal clarifying agent with low yellow index can be mixed with various plastic additives with different functions, which are formed in powders, granulates, tablets, and bars. Examples of plastic additive can be found in fifth edition of *Handbook of Plastic Additives*. For example, the additive may be, but is not limited to, pentaerythritol tetrakis(3-(3,5-di-tert-butyl-4-hydroxyphenyl) propionate) (trade name: IRGANOX 1010, K-NOX 1010), 1,3,5-trimethyl-2,4,6-tris(3,5-di-tert-butyl-4-hydroxybenzyl) benzene) (trade name: IRGANOX 1330, K-NOX 230), tris(2,4-di-tert-butylphenyl) phosphite (trade name: IRGAFOS 168, K-NOX 168), 3, 9-bis(2,4-di-tert-butyl-phenoxy)-2,4,8,10-tetraoxa-3,9-diphosphaspiro[5.5] undecane (trade name: IRGAFOS 126, K-NOX 626), and calcium stearate.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
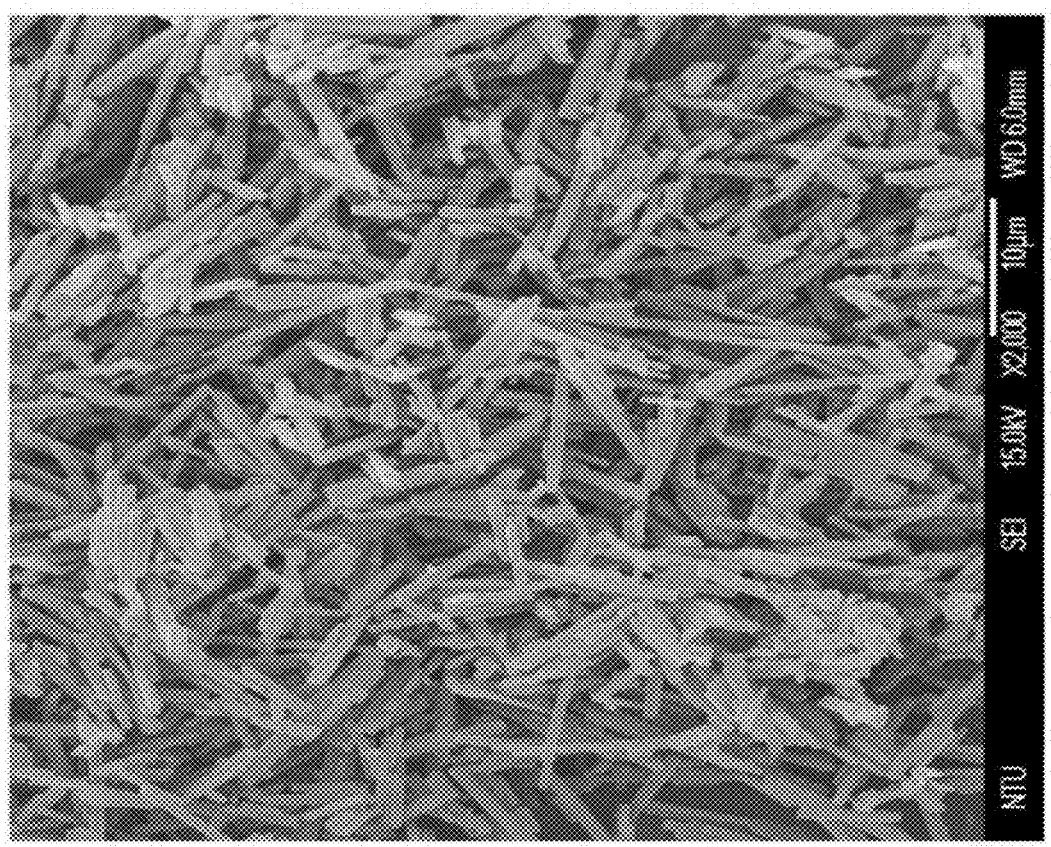
FIG. 1 is an electron microscope image of a powdery diacetal clarifying agent of Example 4 in accordance with the present invention at magnification of 2000×.

Hereinafter, one skilled in the arts can easily realize the advantages and effects of the present invention from the following examples. Therefore, it should be understood that the descriptions proposed herein are just preferable examples for the purpose of illustrations only, not intended to limit the scope of the invention. Various modifications and variations could be made in order to practice or apply the present invention without departing from the spirit and scope of the invention.

The raw materials and detection methods and conditions for the powdery diacetal clarifying agent of Examples 1 to 8 and Comparative Examples 1 to 3 were described as follows.

1. Yield:

The theoretical mass of the powdery diacetal clarifying agent was determined based on the aromatic aldehyde as limiting reagent. The actual mass of the purified and dried product was divided by the theoretical mass and then multiplied by 100% to find the yield.

2. Melting Point (Tm) and Crystallization Temperature (Tc):

The powdery diacetal clarifying agents of Examples 1 to 8 and Comparative Examples 1 to 3 were measured with a differential scanning calorimeter thermal analyzer (Mettler Toledo °, DSC821e). "Mettler Toledo" is a registered trademark of Mettler Toledo Company. The samples were heated to 290° C. from room temperature with a heating rate of 10° C. per minute to determine and record their melting points and crystallization temperatures (also called nucleation temperature).

3. Fourier Transform Infrared Spectroscopy (FTIR):

During the experiments, each sample was mixed with potassium bromide, KBr, in a weight ratio of 1:50 to 1:100 and then pressed after fully grinding to prepare the pressed sample. The FTIR spectra were obtained with a Thermo Nicolet® 330FT-IR spectrometer within the range 4000 $cm^{-1}$ to 400 $cm^{-1}$ to determine the characteristics of the functional groups of the samples. "Nicolet" and "Thermo Nicolet" are registered trademarks of Thermo Nicolet Corporation.

4. Proton Nuclear Magnetic Resonance Spectroscopy ($^1$H-NMR):

Each sample was dissolved in deuterated dimethyl sulfoxide ($d_6$-DMSO), and then analyzed with a Varian NMR-400 spectrometer at 400 MHz. "Varian" is registered trademark of Varian Inc.

Data were reported as the chemical shift (multiplicity, hydrogen atom numbers). The chemical shifts, symbolized by δ, were reported in ppm. Regarding multiplicity, "s" represented singlet, "d" represented doublet, "t" represented triplet, "dd" represented doublet of doublets, "td" represented triplet of doublets, "m" represented multiplet, and "br." represented a broad band.

5. Absorbance (Abs):

Each sample was dissolved in dimethyl sulfoxide to give 1000 ppm solution, and then measured with a UV/VIS Spectrophotometer (JASCO V-550 from JASCO Corporation) to measure the absorbance of the absorption peaks.

6. Ash Content

To determine the ash contained in the powdery diacetal clarifying agents of Examples 1 to 8 and Comparative Examples 1 to 3, 1 gram of precisely weighed sample, as initial weight W0, was placed in the furnace and heated to 600±25° C. for 3 hours to observe the color of the sample. After that, the sample was placed back into the furnace and heated to 800±25° C. for 2 hours until the carbon was fully consumed and the whitish-grey ash was obtained. Subsequently, the whitish-grey ash was moved into the cabinet drier and cooled down to room temperature, and then weighed and recorded its residue weight W1. The analyzed ash content was calculated by the calculation:

$$\frac{W0 - W1}{W0} \times 100\%.$$

7. Purity Determined by Liquid Chromatography (LC):

A Waters 2487 liquid chromatography (LC) equipped with a LiChrospher® 100 column RP-18 was used herein. The column had a length of 25 centimeters, an internal diameter of 4 millimeters, a film thickness of 5 micrometers, and an outer temperature of 30° C. The elution solvent was a mixture of acetonitrile and water (v/v 650/350) of LC-grade and flowed through the column at 0.8 ml/min. The sample powders were dissolved in dimethyl formamide and then diluted with methanol to make the concentration of the samples 1000 ppm, and each injection amount was 20 microliters. "Waters" and "LiChrospher" are registered trademarks of Waters Corporation and Merck KGaA, respectively.

The wavelengths of UV radiations and retention times were different among various compounds, and listed as follows:

1,3:2,4-di(5-methyl-2-thenylidene)-D-sorbitol: 254 nm, 3.32 min;

1,3:2,4-di(4-methyl-benzylidene)-D-sorbitol: 254 nm, 4.93 min;

1,3:2,4-di(3,4-dimethyl-benzylidene)-D-sorbitol: 254 nm, 6.24 min;

1,3:2,4-di(4-n-butyl-benzylidene)-D-sorbitol: 254 nm, 21.32 min.

The aforementioned retention time would slightly vary and shift depending on different LC instruments and columns with different theoretical plate numbers.

8. Residue of Aromatic Aldehyde

A SHIMADZU® gas chromatography GC-2014 equipped with a J&W column HP-1 was used herein. The column had a length of 30 meters, a diameter of 0.32 centimeters, and a film thickness of 0.25 micrometers. The injection temperature was set at 200° C., and the detection temperature was set at 280° C. The column ran with helium gas as a carrier gas with a flow rate of 2 ml per minute. The split ratio was 10:1. During the experiment, the column temperature was set at 100° C. for 3 minutes in the initial state, then heated with a heating rate of 15° C. per minute, and finally kept at 230° C. for 9 minutes. "Shimadzu" is a registered trademark of Shimadzu Corporation.

The retention times were different among various aromatic aldehydes, which were described as follows:

5-methyl-2-thiophenecarboxaldehyde: 5.23 min;
4-methyl benzaldehyde: 4.83 minutes;
3,4-dimethyl benzaldehyde: 6.51 min;
4-n-butyl benzaldehyde: 6.32 min.

Said retention time of the aromatic aldehydes would vary and shift slightly depending on different gas chromatography instruments and columns with different theoretical plate numbers.

In the experiment, 1 gram of different samples of the powdery diacetal clarifying agent was dissolved in 10 ml of methanol, and then ultrasonicated for 30 minutes to obtain a mixture. After filtering the mixture, the filtrates were collected to determine the amounts of aromatic aldehydes. If no absorption peaks of the aromatic aldehydes could be observed, the results were represented as "not detected". Herein, the instrument detection limit was 1 ppm, and the detection limit of the sample was 10 ppm.

9. Yellow Index (YI):

A HunterLab ColorFlex® EZ color meter was employed to measure the YI. Each sample was measured three times to get their average as the YI of the sample. "ColorFlex" is a registered trademark of Hunter Associates Laboratory, Inc.

The higher positive YI represented the sample was yellow in appearance, the lower negative YI represented the sample was blue in appearance, and YI close to zero represented the sample was almost white.

10. Particle Size:

The particle size of the powdery diacetal clarifying agent was measured with a Beckman Coulter LS 13 320/ISO 13320 laser diffraction particle size analyzer with a microvolume module. "Beckman Coulter" is a registered trademark of Beckman Coulter, Inc.

15 mg of each sample was dispersed in ethanol to give 100 ml of solution. After ultra-sonicating the solution for 1 min, the solution was injected into the cell of microvolume module to reach 10% of coverage for the laser particle size analysis to record the particle size with 97% of the particles being smaller than D97 and the median particle size. Each sample was measured three times to get the average.

11. Specification of Aromatic Aldehyde:

i. 5-methyl-2-thiophenecarboxaldehyde (SIGMA-ALDRICH, CAS No. 13679-70-4, purity: 98%);

ii. 4-methyl benzaldehyde (manufactured by Mitsubishi Gas Chemical, Inc., trade name: PTAL, purity>99%);

iii. 3,4-dimethyl benzaldehyde (manufactured by Mitsubishi Gas Chemical, Inc., trade name: 3,4-DBAL, purity>99%);

iv. 4-n-butyl benzaldehyde (manufactured by Mitsubishi Gas Chemical, Inc., trade name: NBBAL, purity>98%); and v. D-sorbitol (manufactured by Shijiazhuang Ruixue Pharmaceutical Co., Ltd., China, purity>99%).

12. Specification of Commercially Available Polyolefin:

i. Globalene ST611: a common polypropylene random copolymer, manufactured by Taiwan LCY Chemical Industry Corporation, melt flow index (230° C., 2.16 kg): 1.8 grams per 10 minutes;

ii. Tairipro T3002: blow molding grade polypropylene random copolymer, manufactured by Formosa Chemicals & Fibre Corporation, melt flow index (230° C., 2.16 kg): 1.6 grams per 10 minutes;

iii. Basell Moplen RP242G (LyondellBasell Industries): chemical and impact resistant grade polypropylene random copolymer with low melt flow index, manufactured by HMC Polymer in Thailand, melt flow index (230° C., 2.16 kg): 0.15 grams per 10 minutes;

iv. Borealis RB307MO: blow molding grade polypropylene random copolymer, manufactured by Borealis Company, melt flow index (230° C., 2.16 kg): 1.5 grams per 10 minutes;

v. Titanpro SM198: injection and blow molding grade polypropylene random copolymer, manufactured by Titan Chemicals Corp. Bhd., melt flow index (230° C., 2.16 kg): 1.6 grams per 10 minutes; and vi. Engage 8480: ethylene-octene copolymer, manufactured by Dow Chemical Company, melt flow index (190° C., 2.16 kg): 1 gram per 10 minutes.

13. Commercial Product of Diacetal Clarifying Agent for Comparison:

i. 1,3:2,4-di(4-methyl-benzylidene)-D-sorbitol (MDBS), e.g., commercial product Millad® 3940, manufactured by Milliken Chemical Company, or commercial product LM30, manufactured by New Japan Chemical co., Ltd; and ii. 1,3:2,4-di(3,4-dimethyl-benzylidene)-D-sorbitol (DM-DBS) e.g., commercial product Millad® 3988i, manufactured by Milliken Chemical Company, or commercial product Geniset® DXR, manufactured by Rita Corporation.

Example 1

In the instant example, a powdery diacetal clarifying agent of 1,3:2,4-di(5-methyl-2-thenylidene)-D-sorbitol was prepared through the following steps.

(a) A 500 ml four-necked cylindrical shaped reaction flask equipped with a thermometer, a nitrogen inlet, and a mechanical stirrer was charged with D-sorbitol (19.0 grams, 0.104 moles), methanesulfonic acid (0.4 grams), 5-methyl-2-thiophenecarboxaldehyde (25.0 grams, 0.198 moles), and methanol (150 grams) and then reacted at room temperature for 45 hours, so as to form a first reaction mixture.

(b) The first reaction mixture was filtered to remove the mother liquor, and then added with new 100 grams of methanol and 10% of sodium hydroxide solution into the reaction flask slowly to neutralize the solution to pH>7. Subsequently, potassium borohydride powders (0.3 grams, purity>96%) and Ultramarine Blue (0.15 grams, CAS No. 57455-37-5) were added in the first reaction mixture and stirred for 1 hour to obtain a second reaction solution.

(c) The second reaction solution was filtered to collect the solid precipitate from the second reaction solution. Then the solid precipitate was washed with 40 wt % methanol solution, and then dried and ground to obtain nearly white powdery diacetal clarifying agent of 1,3:2,4-di(5-methyl-2-thenylidene)-D-sorbitol (28.4 grams, yield 72.1% calculated from 39.4 grams of theoretical mass). Based on the total weight of the produced powdery diacetal clarifying agent, the amount of the Ultramarine Blue was about 0.5 wt %. The produced powdery diacetal clarifying agent of Example 1 had the following characteristics:

i. Melting point: 198.78° C.

ii. Data of $^1$H-NMR spectrum (400 MHz, $d_6$-DMSO): δ6.89 (d, 2H), 6.69 (d, 2H), 5.79 (s, 2H), 4.79 (d, 1H), 4.41 (t, 1H), 4.17-4.00 (m, 3H), 3.88 (s, 1H), 3.80-3.78 (m, 1H), 3.75-3.65 (m, 1H), 3.60-3.55 (m, 1H), 3.50-3.40 (m, 1H), 2.42 (s, 6H).

iii. Data of FTIR spectrum: λ3222, 2918, 2866, 1497, 1449, 1398, 1371, 1341, 1266, 1227, 1164, 1133, 1110, 1081, 1167, 1021, 1000, 960, 884, 858, 802, 769, 667, 614, 570, 544, 486 cm$^{-1}$.

iv. Data of UV/VIS spectrum: absorbance at 262 nm: 2.1820; absorbance at 292 nm: 1.0658; absorbance at 649 nm: 0.0036.

v. Ash content: 0.51%.

vi. Purity determined by LC: 99.6%.

vii. GC analysis result of the residue of aromatic aldehyde: no 5-methyl-2-thiophenecarboxaldehyde was detected.

Comparative Example 1

A conventional clarifying agent composition containing 1,3:2,4-di(5-methyl-2-thenylidene)-D-sorbitol and an organosilane treated fume silica was prepared as follows, which could be found from Example 4 of Taiwan Patent No. 1353998.

(a) A 1 L four-necked cylindrical shaped reaction flask equipped with a thermometer, a nitrogen inlet, and a mechanical stirrer was charged with D-sorbitol (20.0 grams, 0.110 moles), methanesulfonic acid (1.00 grams), 5-methyl-2-thiophenecarboxaldehyde (25.0 grams, 0.198 moles), and methanol (200 ml) and then reacted at room temperature for 48 hours, so as to form a first reaction mixture.

(b) The first reaction mixture was then neutralized to pH 8 to pH9 with 4% of sodium hydroxide solution, and added with an organosilane treated fume silica (3.0 grams, CAB-O-SIL® TS-720) to form a second reaction mixture.

(c) The second reaction mixture was then filtered to collect a precipitate product. Then the precipitate product was washed with 40% of methanol solution, dried and ground to give light yellow to white 1,3:2,4-di(5-methyl-2-thenylidene)-D-sorbitol (30.7 grams), having the following characteristics:

i. Melting point: 212.5° C.
ii. Data of FTIR spectrum: λ3287, 2919, 1678, 1498, 1457, 1398, 1377, 1341, 1265, 1226, 1164, 1081, 1056, 1021, 960, 894, 802, 769, 671, 644, 614, 584, 485 cm$^{-1}$.
iii. Ash content: 9.2%.
iv. Purity determined by LC: 93.70%.

Example 2

In the instant example, a powdery diacetal clarifying agent of 1,3:2,4-di(3,4-dimethyl-benzylidene)-D-sorbitol was prepared through the following steps.

(a) An 80 L small reaction flask equipped with a thermometer, a nitrogen inlet, and a mechanical stirrer was charged with D-sorbitol (4000 grams, 22 moles), methanesulfonic acid (100 grams), 3,4-dimethyl benzaldehyde (5300 grams, 39.5 moles), and methanol (40 L) and then reacted at room temperature for 42 hours, so as to form a first reaction mixture.

(b) The first reaction mixture was filtered to remove the mother liquor, and added with new 20 L of methanol Subsequently, 12% of potassium borohydride solution (200 grams) and Ultramarine Blue (1.28 grams) were slowly added into the first reaction mixture and stirred for 1 hour to obtain a second reaction solution.

(c) The second reaction solution was filtered to collect the solid precipitate from the second reaction solution. Then the solid precipitate was washed with 40 wt % methanol solution and dried to give white powdery diacetal clarifying agent of 1,3:2,4-di(3,4-dimethyl-benzylidene)-D-sorbitol (6613 grams, yield 80.8% calculated from 8185 grams of theoretical mass). Based on the total weight of the produced powdery diacetal clarifying agent, the amount of the Ultramarine Blue was about 0.02 wt %. The produced powdery diacetal clarifying agent of Example 2 had the following characteristics:

i. Melting point: 274.45° C. and crystallization temperature: 227.99° C.
ii. Data of $^1$H-NMR spectrum (400 MHz, d$_6$-DMSO): δ 7.23-7.11 (m, 6H), 5.58 (s, 2H), 4.81 (d, 1H), 4.41 (t, 1H), 4.14-4.09 (m, 3H), 3.88 (s, 1H), 3.81-3.74 (m, 2H), 3.65-3.57 (m, 1H), 3.50-3.40 (m, 1H), 2.24 (s, 12H).
iii. Data of FTIR spectrum: λ3212, 2939, 2858, 1505, 1453, 1400, 1372, 1340, 1262, 1245, 1213, 1168, 1125, 1098, 1068, 1026, 998, 898, 881, 857, 824, 790, 769, 714, 668, 632, 578, 543, 475, 436 cm$^{-1}$.
iv. Data of UV/VIS spectrum: absorbance at 265 nm: 1.5606; absorbance at 649 nm: 0.0007.
v. Ash content: 0.01%.
vi. Purity determined by LC: 99.75%.
vii. GC analysis result of the residue of aromatic aldehyde: no 3,4-dimethyl benzaldehyde was detected.

Examples 3 to 6

Each of the powdery diacetal clarifying agents of 1,3:2,4-di(3,4-dimethyl-benzylidene)-D-sorbitol of Examples 3 to 6 was prepared by the method as described in Example 2. The differences between Examples 3 to 6 were that various inorganic silicon-containing agents in different amounts were employed in Examples 3 to 6. That is, Ultramarine Blue (CAS No. 57455-37-5) was used as the inorganic silicon-containing agent in the preparation of Examples 3 to 5; and Tixolex® 17 (CAS No. 1344-00-9) was used as the inorganic silicon-containing agent in the preparation of Example 6. The respective amounts of the inorganic silicon-containing agents used in Examples 3 to 6 were listed in Table 1 below. The white powdery diacetal clarifying agent prepared by Examples 3 to 6 did not release stinking odor, and none of them could be detected to contain 3,4-dimethyl benzaldehyde.

According to the detection methods as described above, the characteristics including yield, melting point, crystallization temperature, ash content, and absorbance observed from UV/VIS spectrum were described below and listed in Table 1.

Besides, commercial products Millad® 3988i and Geniset® DXR, i.e., 1,3:2,4-di(3,4-dimethyl-benzylidene)-D-sorbitol free of Ultramarine Blue, were used for comparison, and their characteristics were also listed in Table 1 below.

TABLE 1 the amounts of inorganic silicon-containing agents (unit: grams), yield (unit: %), ash contents (unit: %), melting points (Tm, unit: ° C.) and crystallization temperatures (Tc, unit: ° C.) measured by the differential scanning calorimeter thermal analyzers, and absorbances (Abs) at 262-265 nm and 649 nm obtained from UV/VIS spectra of Examples 3 to 6 and commercial products Millad ® 3988i and Geniset ® DXR.

|  | Amount | Yield | Tm (° C.) | Tc (° C.) | Ash Content | Abs at 262-265 nm | Abs at 649 nm |
|---|---|---|---|---|---|---|---|
| Example 3 | 13.2 | 82.5 | 274.16 | 222.57 | 0.21 | 1.6672 | 0.0040 |
| Example 4 | 33.0 | 84.8 | 274.86 | 227.47 | 0.55 | 1.5438 | 0.0102 |
| Example 5 | 66.0 | 86.7 | 277.29 | 246.76 | 0.96 | 1.5160 | 0.0216 |
| Example 6 | 33.0 | 83.2 | 274.34 | 226.33 | 0.47 | 1.4765 | −0.0002 |
| Millad ® 3988i | n/a | n/a | 272.00 | 192.36 | 3.10 | 1.4010 | 0.0007 |
| GENISET ® DXR | n/a | n/a | 273.29 | 213.46 | 0.01 | 1.5778 | 0.0016 |

In addition to the characteristics as shown in Table 1 above, the other analysis results of the powdery diacetal clarifying agent of Examples 3 to 6 were listed as follows.

I. Analysis results of Example 3:
  i. Purity determined by LC: 99.69%.
  ii. Data of FTIR spectrum: λ3212, 3014, 2939, 2858, 1505, 1452, 1400, 1371, 1339, 1308, 1262, 1245, 1213, 1168, 1126, 1097, 1058, 1026, 997, 898, 881, 857, 824, 790, 769, 713, 668, 632, 578, 543, 436 cm$^{-1}$.
  iii. Amount of Ultramarine Blue: 0.2 wt % based on the total weight of the produced powdery diacetal clarifying agent of Example 3
II. Analysis results of Example 4:
  i. Purity determined by LC: 99.66%.
  ii. Data of FTIR spectrum: λ3213, 2939, 2859, 1505, 1453, 1400, 1371, 1340, 1262, 1247, 1213, 1168, 1125, 1098, 1058, 1026, 998, 898, 881, 857, 824, 790, 770, 668, 632, 578, 543, 436 cm$^{-1}$.
  iii. Amount of Ultramarine Blue: 0.5 wt % based on the total weight of the produced powdery diacetal clarifying agent of Example 4.
III. Analysis results of Example 5:
  i. Purity determined by LC: 99.69%.
  ii. Data of FTIR spectrum: λ3216, 2939, 2859, 1619, 1505, 1453, 1400, 1371, 1340, 1261, 1246, 1212, 1168, 1125, 1098, 1057, 1026, 998, 898, 881, 858, 824, 790, 770, 713, 669, 632, 579, 544, 437 cm$^{-1}$.
  iii. Amount of Ultramarine Blue: 1.0 wt % based on the total weight of the produced powdery diacetal clarifying agent of Example 5.
IV. Analysis results of Example 6:
  i. Purity determined by LC: 99.68%.
  ii. Data of FTIR spectrum: λ3215, 2939, 2858, 1505, 1452, 1400, 1371, 1340, 1327, 1308, 1262, 1246, 1213, 1170, 1125, 1099, 1057, 1026, 998, 981, 899, 881, 858, 824, 790, 770, 578, 543, 436 cm$^{-1}$.
  iii. Amount of Tixolex® 17: 0.5 wt % based on the total weight of the produced powdery diacetal clarifying agent of Example 6.

Comparative Example 2

The powdery diacetal clarifying agent of 1,3:2,4-di(3,4-dimethyl-benzylidene)-D-sorbitol of the instant comparative example was prepared through the following steps. No hydrogenating agent and inorganic silicon-containing agent was employed in the instant comparative example.

(a) An 80 L small reaction flask equipped with a thermometer, a nitrogen inlet, and a mechanical stirrer was charged with D-sorbitol (4000 grams, 22 moles), methanesulfonic acid (100 grams), 3,4-dimethyl benzaldehyde (5300 grams, 39.5 moles), and methanol (40 L) and then reacted at room temperature for 42 hours, so as to form a first reaction mixture.

(b) The first reaction mixture was filtered to remove the mother liquor, added with new 30 L of methanol, and then neutralized with 4% of sodium hydroxide solution to pH8 to pH 9 to obtain a mixing solution.

(c) The mixing solution was stirred for 1 hour and then filtered to obtain a precipitate product. Then the precipitate product was washed with 40 wt % methanol solution and dried to give white powdery diacetal clarifying agent of 1,3:2,4-di(3,4-dimethyl-benzylidene)-D-sorbitol (6450 grams, yield 78.8% calculated from 8185 grams of theoretical mass).

The produced powdery diacetal clarifying agent of Comparative Example 2 had the following characteristics:
  i. Melting point: 274.86° C. and crystallization temperature: 227.47° C.
  ii. Data of FTIR spectrum: λ3212, 3015, 2953, 2939, 2857, 1506, 1453, 1400, 1372, 1340, 1327, 1308, 1262, 1246, 1213, 1170, 1125, 1115, 1098, 1068, 1057, 1026, 998, 981, 935, 899, 881, 858, 824, 790, 769, 713, 669, 632, 579, 543, 436 cm$^{-1}$.
  iii. Ash content: 0.01%.
  iv. Purity determined by LC: 98.62%.
  v. Residue of aromatic aldehyde measured by GC analysis: 120 ppm of 3,4-dimethyl benzaldehyde.

Example 7

In the instant example, a powdery diacetal clarifying agent of 1,3:2,4-di(4-methyl-benzylidene)-D-sorbitol was prepared through the following steps.

(a) A 1 L four-necked cylindrical shaped reaction flask equipped with a thermometer, a nitrogen inlet, and a mechanical stirrer was charged with D-sorbitol (56.78 grams, 0.312 moles), camphor sulfonic acid (1.8 grams), 4-methyl benzaldehyde (68.1 grams, 0.567 moles), and methanol (500 grams) and then reacted at room temperature for 40 hours, so as to form a first reaction mixture.

(b) The first reaction mixture was filtered to remove the mother liquor, and then added with new 250 grams of methanol and neutralized to pH 8 under stirring. Subsequently, potassium borohydride powders (1 gram, purity>96%) were added in the first reaction mixture and stirred for 30 minutes, and then added with 4 wt % Laponite® RD aqueous suspension (10 grams, CAS No. 227605-22-3) and stirred for 1 hour to obtain a second reaction solution.

(c) The second reaction solution was filtered to collect the solid precipitate. Then the precipitate product was washed with 40 wt % of methanol solution, dried and ground to give nearly white powdery diacetal clarifying agent of 1,3:2,4-di(4-methyl-benzylidene)-D-sorbitol (86.5 grams, yield 78.9% calculated from 109.6 grams of theoretical mass). Based on the total weight of the produced powdery diacetal clarifying agent, the amount of Laponite® RD was about 0.46 wt %. The produced powdery diacetal clarifying agent of Example 7 had the following characteristics:
  i. Melting point: 258.28° C. and crystallization temperature: 202.41° C.
  ii. Data of $^1$H-NMR spectrum (400 MHz, d$_6$-DMSO): δ7.34-7.30 (dd, 4H), 7.19-7.15 (dd, 4H), 5.59 (s, 2H), 4.81 (d, 1H), 4.39 (t, 1H), 4.20-4.09 (m, 3H), 3.88 (s, 1H), 3.81-3.78 (m, 1H), 3.75-3.70 (m, 1H), 3.59-3.54 (m, 1H), 3.42-3.38 (m, 1H), 2.28 (s, 6H).
  iii. Data of FTIR spectrum: λ3222, 3031, 2956, 2862, 1619, 1517, 1450, 1400, 1371, 1342, 1328, 1312, 1264, 1168, 1098, 1057, 1022, 982, 944, 884, 835, 818, 785, 778, 764, 661, 617, 599, 560, 543, 482 cm$^{-1}$.
  iv. Data of UV/VIS spectrum: absorbance at 262 nm: 1.0152; and absorbance at 649 nm: 0.0048.
  v. Ash content: 0.42%.
  vi. Purity determined by LC: 99.27%.
  vii. GC analysis result of the residue of aromatic aldehyde: no 4-methyl benzaldehyde was detected.

Comparative Example 3

A powdery diacetal clarifying agent of 1,3:2,4-di(4-methyl-benzylidene)-D-sorbitol was prepared by using an acidic inorganic silicon-containing agent as dispersant. The preparation comprised the following steps.

(a) A 1 L four-necked cylindrical shaped reaction flask equipped with a thermometer, a nitrogen inlet, and a mechanical stirrer was charged with D-sorbitol (56.78 grams, 0.312 moles), methanesulfonic acid (1.8 grams), 4-methyl benzaldehyde (68.1 grams, 0.567 moles), and methanol (500 grams) and then reacted at room temperature for 40 hours, so as to form a first reaction mixture.

(b) The first reaction mixture was filtered to remove the mother liquor, and added with new 250 grams of methanol and neutralized to pH 8 under stirring. Subsequently, sodium borohydride powders (0.5 grams, purity>96%) were added in the first reaction mixture and stirred for 30 minutes, and then added with 0.2 grams of acid clay (manufactured by Clariant Company, trade name: TONSIL OPTIMUM 230FF, 10% aqueous suspension of pH 2 to pH 3) to form a second reaction solution.

(c) The second reaction solution was filtered to collect the solid precipitate from the second reaction solution. Then the solid precipitate was washed with 40 wt % methanol solution, and then dried and ground to obtain nearly white powdery diacetal clarifying agent of 1,3:2,4-di(4-methyl-benzylidene)-D-sorbitol (85.3 grams, yield 77.8% calculated from 109.6 grams of theoretical mass), which released slight odor of aldehyde. Based on the total weight of the produced powdery diacetal clarifying agent, the amount of the acid clay was about 0.2 wt %. The produced powdery diacetal clarifying agent of Comparative Example 3 had the following characteristics:

i. Data of FTIR spectrum: λ3221, 2956, 2941, 2862, 1619, 1517, 1450, 1400, 1371, 1342, 1328, 1311, 1264, 1226, 1168, 1133, 1098, 1056, 1022, 982, 944, 884, 835, 818, 785, 764, 715, 661, 616, 599, 560, 543, 515, 482, 431 $cm^{-1}$.

ii. Data of UV/VIS spectrum: absorbance at 262 nm: 1.1494; and absorbance at 649 nm: 0.0787.

iii. Ash content: 2.35%.

iv. Purity determined by LC: 94.65%.

v. GC analysis result of the residue of aromatic aldehyde: no 4-methyl benzaldehyde was detected.

Example 8

In the instant example, a powdery diacetal clarifying agent of 1,3:2,4-di(4-n-butyl-benzylidene)-D-sorbitol was prepared through the following steps.

(a) A 1 L four-necked cylindrical shaped reaction flask equipped with a thermometer, a nitrogen inlet, and a mechanical stirrer was charged with D-sorbitol (56.78 grams, 0.312 moles), camphor sulfonic acid (1.8 grams), 4-n-butyl benzaldehyde (91.8 grams, 0.567 moles), and methanol (613 grams) and then reacted at room temperature for 48 hours, so as to form a first reaction mixture.

(b) The first reaction mixture was filtered to remove the mother liquor, and then added with new 300 grams of methanol and neutralized to pH 8 under stirring. Subsequently, potassium borohydride powders (1.1 grams, purity>96%) and Ultramarine Blue (0.6 grams) were slowly added into the first reaction mixture and stirred for 1 hour to obtain a second reaction solution.

(c) The second reaction solution was filtered to collect the solid precipitate from the second reaction solution. Then the solid precipitate was washed with 40 wt % methanol solution, and then dried and ground to obtain nearly white powdery diacetal clarifying agent of 1,3:2,4-di(4-n-butyl-benzylidene)-D-sorbitol (108.4 grams, yield 81.35% calculated from 133.2 grams of theoretical mass). Based on the total weight of the produced powdery diacetal clarifying agent, the amount of the Ultramarine Blue was about 0.6 wt %. The produced powdery diacetal clarifying agent of Example 8 had the following characteristics:

i. Melting point: 237.07° C. and crystallization temperature: 208.36° C.

ii. Data of $^1$H-NMR spectrum (400 MHz, $d_6$-DMSO): δ 7.40-7.30 (dd, 4H), 7.20-7.15 (dd, 2H), 5.61 (s, 2H), 4.81 (d, 1H), 4.41 (t, 1H), 4.20-4.09 (m, 3H), 3.88 (s, 1H), 3.85-3.80 (m, 1H), 3.79-3.70 (m, 1H) 3.62-3.58 (m, 1H), 3.42-3.38 (m, 1H), 2.58 (t, 4H), 1.60-1.45 (m, 4H), 1.35-1.25 (m, 4H), 0.90 (t, 6H).

iii. Data of FTIR spectrum: λ3239, 2955, 2932, 2858, 1618, 1516, 1458, 1420, 1399, 1370, 1341, 1328, 1310, 1263, 1223, 1167, 1099, 1054, 1018, 980, 945, 883, 831, 768, 727, 663, 639, 622, 574, 554, 533 $cm^{-1}$.

iv. Data of UV/VIS spectrum: absorbance at 262 nm: 0.8117; absorbance at 649 nm: 0.0044.

v. Ash content: 0.53%.

vi. Purity determined by LC: 98.15%.

vii. GC analysis result of the residue of aromatic aldehyde: no 4-n-butyl benzaldehyde was detected.

Test Example 1: Particle Size and Yellow Index

In the instant test example, the powdery diacetal clarifying agents of Examples 1 to 8 and Comparative Examples 2 and 3, commercial products Millad® 3988i, Geniset® DXR, and Millad® 3940 were used as samples to measure their particle sizes and color appearances.

Each of the samples was ground with RT-25 airflow-type ultrafine powder and high-speed grinder machine, and then measured its particle size distribution with a laser diffraction particle size analyzer. The results of D97 and median particle size were listed in Table 2.

Further, each of the samples was thermally aged at 200° C. in a circulation oven for 2 hours to determine the degree of the yellowing. The yellow index of each sample at room temperature, about 25° C. to 30° C., and the yellow index of each sample after thermal aging were measured for comparison. The results were listed in Table 2.

TABLE 2

D97, median particle sizes, yellow indices at room temperature ($YI_0$), and yellow indices after 2 hours thermal aging ($YI_1$) of the powdery diacetal clarifying agents of Examples 1 to 8, Comparative Examples 2 and 3, commercial products Millad® 3988i, Geniset® DXR, and Millad® 3940.

| Sample No. | D97 | Median Particle Size | $YI_0$ | $YI_1$ |
|---|---|---|---|---|
| Example 1 | 23.9 μm | 5.87 μm | −0.44 | +0.71 |
| Example 2 | 13.0 μm | 3.26 μm | −0.44 | +0.71 |
| Example 3 | 10.3 μm | 3.25 μm | −9.07 | −4.11 |
| Example 4 | 10.1 μm | 3.18 μm | −11.68 | −9.02 |
| Example 5 | 10.5 μm | 3.32 μm | −14.00 | −13.12 |
| Example 6 | 15.9 μm | 3.01 μm | +0.82 | +3.77 |
| Example 7 | 16.4 μm | 3.85 μm | −0.48 | +0.65 |
| Example 8 | 34.5 μm | 10.8 μm | +0.16 | +2.50 |
| Comparative Example 2 | 43.9 μm | 17.6 μm | +6.12 | +9.03 |
| Comparative Example 3 | 24.1 μm | 4.74 μm | −0.48 | n/a (brown gel) |
| Millad® 3988i | 24.9 μm | 4.51 μm | +1.53 | +5.01 |
| Geniset® DXR | 22.2 μm | 6.77 μm | +1.92 | +5.70 |
| Millad® 3940 | 38.9 μm | 13.1 μm | +3.06 | +4.25 |

According to Table 2, each of the powdery diacetal clarifying agents of Examples 1 to 8 had a smaller D97 than those of Comparative Example 2 and the foresaid commercial products. Similarly, each of the powdery diacetal clarifying agents of Examples 1 to 8 had a smaller median particle size than those of Comparative Example 2 and the foresaid commercial products. For the powdery diacetal clarifying agents of 1,3:2,4-di(4-methyl-benzylidene)-D-sorbitol, both D97 and median particle size of Example 7 were smaller than those of Comparative Example 3, respectively. The results indicate that the inorganic silicon-containing compound of pH 6 to pH 12 is useful to improve the dispersability of the powdery diacetal clarifying agent, such that the powdery diacetal clarifying agents of Examples 1 to 8 have a dispersability superior to those of Comparative Examples 2 and 3 and the commercial products.

Regarding the degree of yellowing, the $YI_0$ of the powdery diacetal clarifying agents of Examples 1 to 8 was less than the $YI_0$ of Comparative Example 2 and the foresaid commercial products, and so was $YI_1$. According to the comparison results of Example 7 and Comparative Example 3, the powdery diacetal clarifying agent of Comparative Example 3 had turned into brown gel after thermal aging; however, the diacetal clarifying agent of Example 7 still appeared nearly white. The results indicate that the powdery diacetal clarifying agents of Examples 1 to 8 also have a color stability superior to those of Comparative Examples 2 and 3 and the commercial products, and thus the occurrence of yellowing during plastics processing can be effectively inhibited by using the powdery diacetal clarifying agent of the present invention.

Test Example 2: Dispersability

In the instant test example, the powdery diacetal clarifying agents of Example 4 and Comparative Example 2 and of commercial product Geniset® DXR were observed with an electronic microscope (field-emission scanning electron microscope (FE-SEM), JOEL JSM-6700F) to compare their dispersability. The electron microscope images of Example 4, Comparative Example 2, and commercial product Geniset® DXR at magnification of 2000× were shown in FIGS. 1 to 3 respectively, and their electron microscope images at magnification of 5000× were shown in FIGS. 4 to 6.

Figure 2:
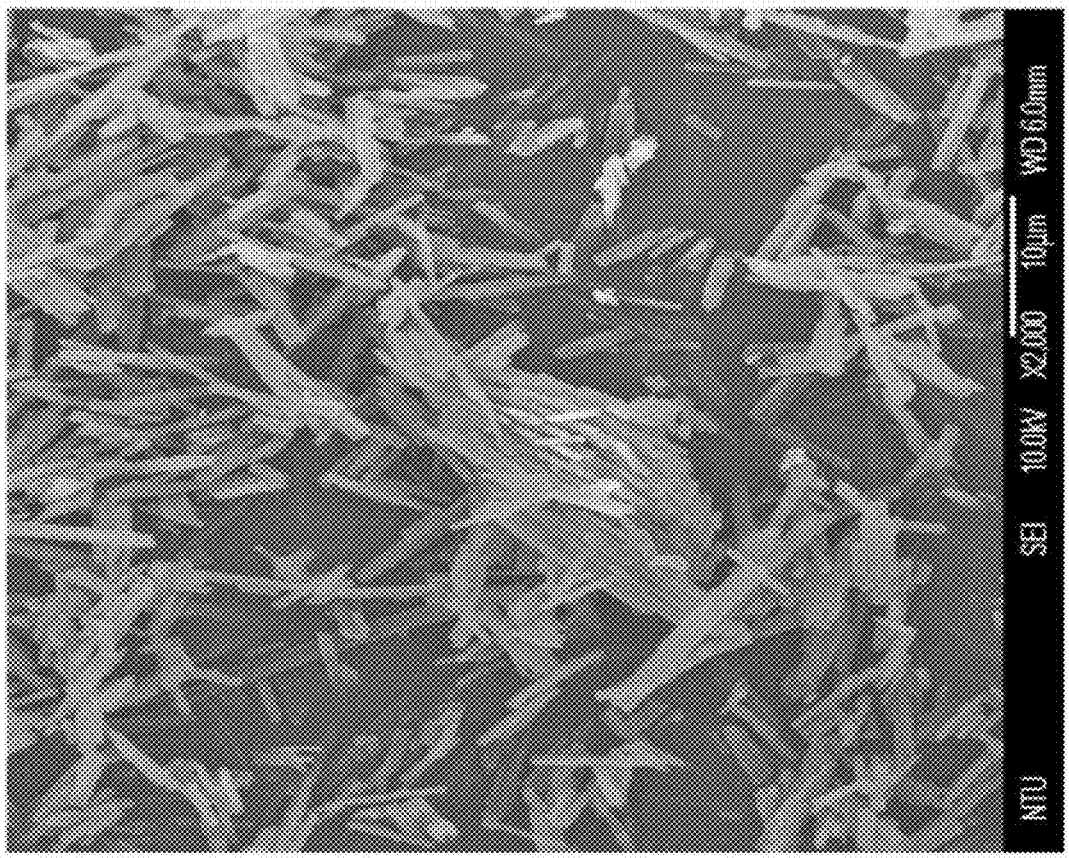
FIG. 2 is an electron microscope image of a powdery diacetal clarifying agent of Comparative Example 2 at magnification of 2000×.
Figure 3:
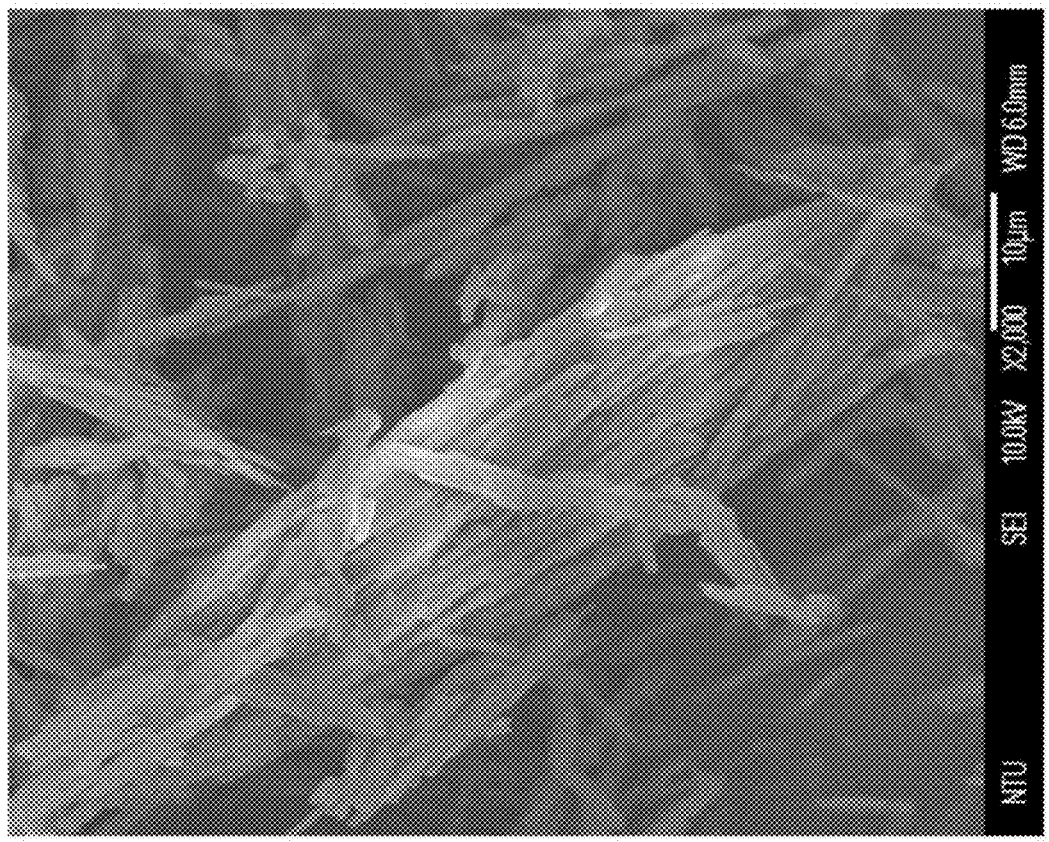
FIG. 3 is an electron microscope image of a commercial product (GENISET DXR) at magnification of 2000×.
Figure 4:
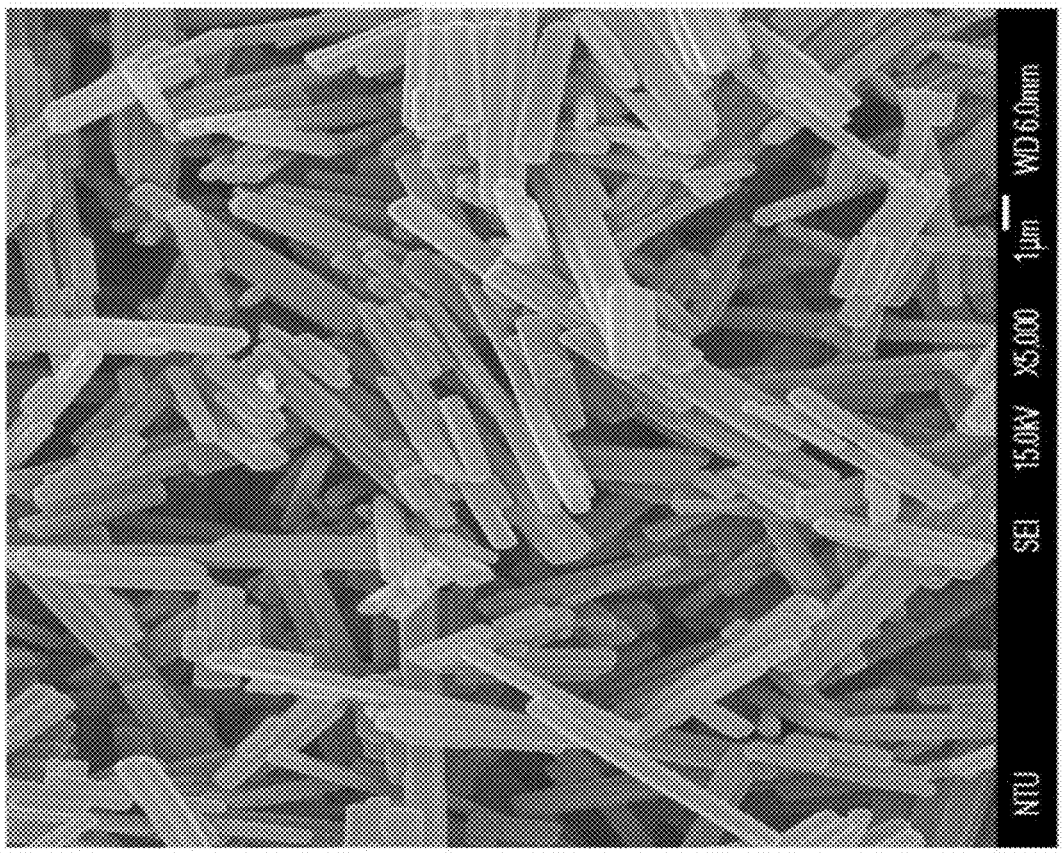
FIG. 4 is an electron microscope image of the powdery diacetal clarifying agent of Example 4 in accordance with the present invention at magnification of 5000×.
Figure 5:
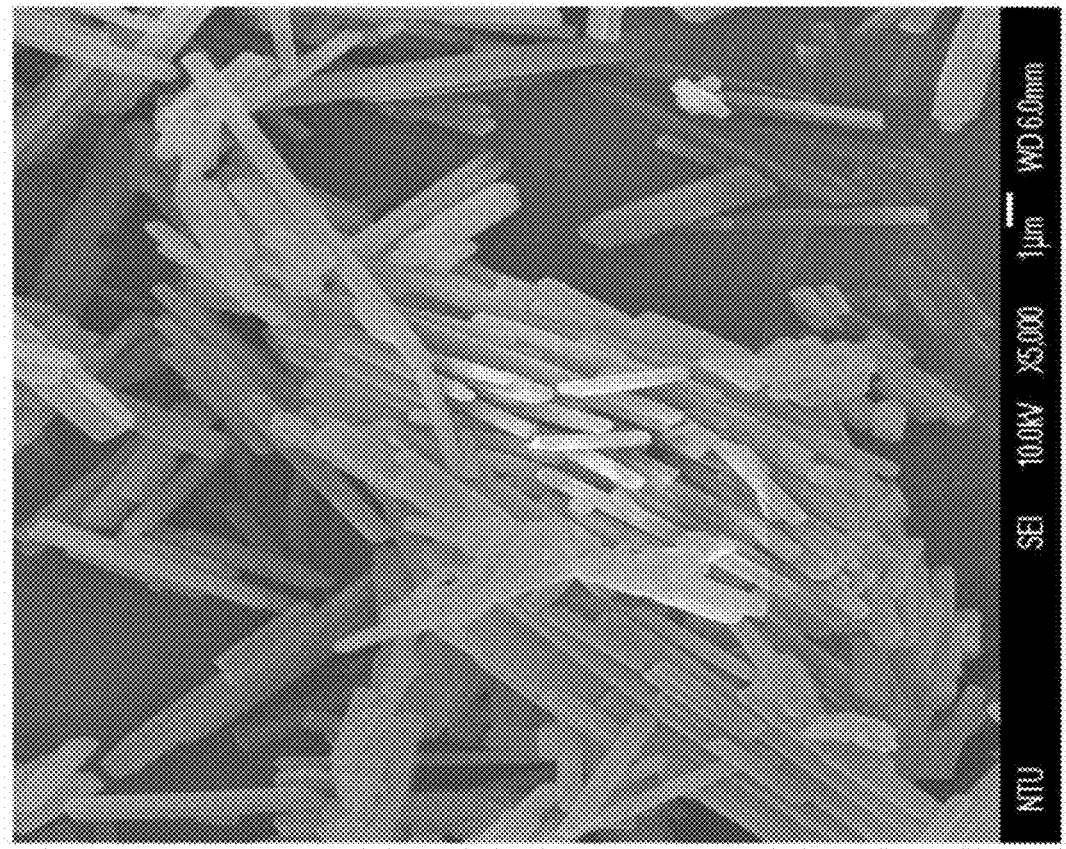
FIG. 5 is an electron microscope image of the powdery diacetal clarifying agent of Comparative Example 2 at magnification of 5000×.
Figure 6:
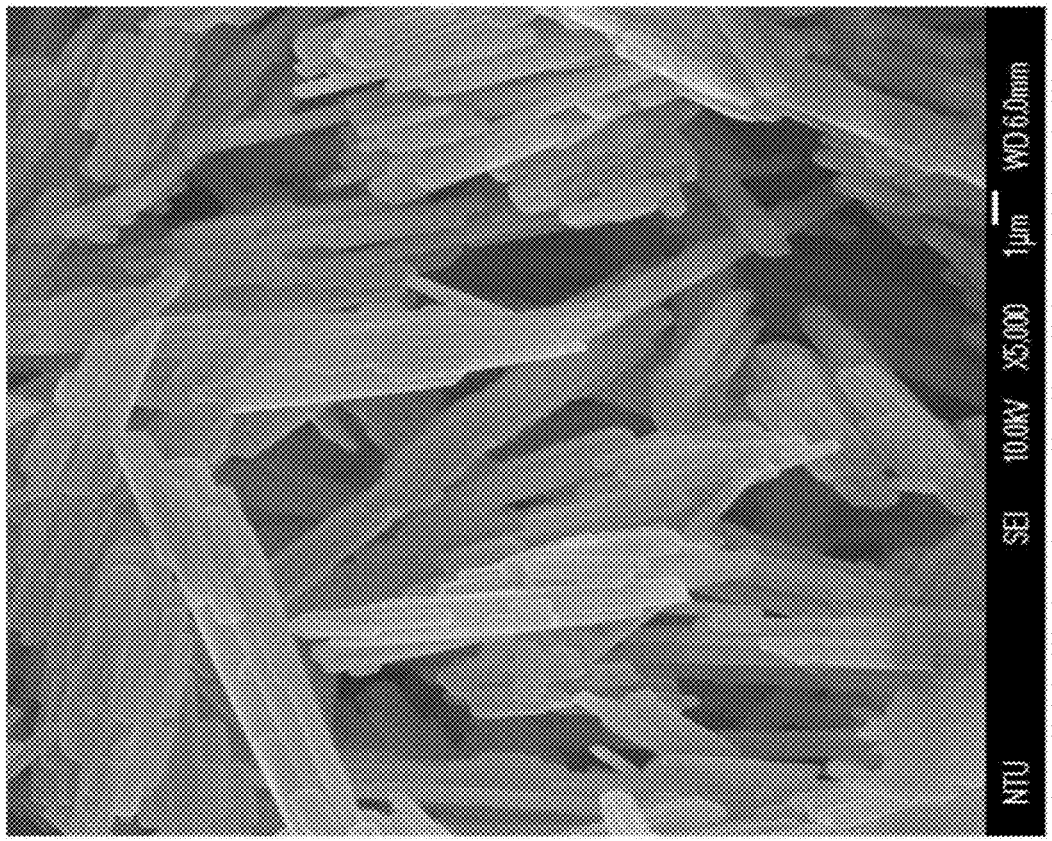
FIG. 6 is an electron microscope image of the commercial product (Geniset® DXR) at magnification of 5000×.

In comparison with FIGS. 2, 3, 5, and 6, the powdery diacetal clarifying agent of Example 4 had the best dispersability as shown in FIGS. 1 and 4. With reference to FIGS. 2 and 5, a part of powders significantly aggregated in the powdery diacetal clarifying agent of Comparative Example 2. With reference to FIGS. 3 and 6, the aggregation occurring in the commercial product Geniset® DXR was more severe than the foresaid powdery diacetal clarifying agent.

It demonstrates that the inorganic silicon-containing compound provides a significant effect to improve the dispersability of the powdery diacetal clarifying agent and prevent aggregation.

Test Example 3: Flowability and Operability

In the instant test example, the powdery diacetal clarifying agent prepared by Example 4 was ground again with RT-25 airflow-type ultrafine powder and high-speed grinder machine to form the ground sample of Example 4.

In the test example, the ground sample of Example 4 and commercial product Millad® 3988i were analyzed with BT-1000 powder flowability tester according to the manual to measure their flowabilities. The flowability was represented by the following data.

i. angle of repose, a smaller angle of repose indicated a better powder flowability;
    ii. angle of spatula, a smaller angle of spatula indicated a better powder flowability;
    iii. collapse angle: an angle at which powders placed for measurement of angle of repose were collapsed by an external force;
    iv. angle of difference: the difference between the angle of repose and the collapse angle, a larger angle of difference indicated a better powder flowability.

"Dispersability" meant the degree that the powders dispersed in air, a larger dispersability indicating the powders were more likely to disperse. 10 grams of samples were weighed and added into the inlet of equipment through the metal funnel. Then the outlet was opened immediately to allow the samples to fall freely down to the stock pan. After that, the stock pan was moved out and weighed to record the weight (m) of the powders in the stock pan. The foresaid steps were repeated twice to get the average of m, and then the dispersability was calculated by the following equation.

$$\text{Dispersability} = \frac{10 - m}{10} \times 100\%$$

The results of the flowability, including angle of repose, angle of spatula, collapse angle, angle of difference, dispersability of the powders were listed in Table 3. Besides, the operability of the sample was also recorded in Table 3.

TABLE 3 flowability, dispersability, and operability of the powdery diacetal clarifying agent of Example 4 and commercial product Millad ® 3988i.

|  | Millad ® 3988i | Example 4 |
| --- | --- | --- |
| Angle of Repose | 43.66° | 51.66° |
| Angle of Spatula | 48.50° | 51.00° |
| Collapse Angle | 36.00° | 38.66° |
| Angle of Difference | 7.65° | 13.00° |
| Dispersability | 6.30% | 3.39% |
| Operability | Easy feeding, powders did not adhere onto the metal funnel, and severe powder suspension in air. | Easy feeding and powders did not adhere onto the metal funnel |

Test Example 4: Powder Flow Function

The powder flow functions of the powdery diacetal clarifying agents of Example 4 and Comparative Example 2 were installed in a 236 cc standard plate and measured with a Think Brookfield PFT® powder flow tester from Brookfield Engineering Laboratories, Inc., Powder Flow Pro V1.3 Build 23 software. Said powder flow tester was provided with a consolidation stress and an unconfined failure strength (kPa) to allow the powders to flow, and the test was operated according to the manual of the powder flow tester.

Figure 7:
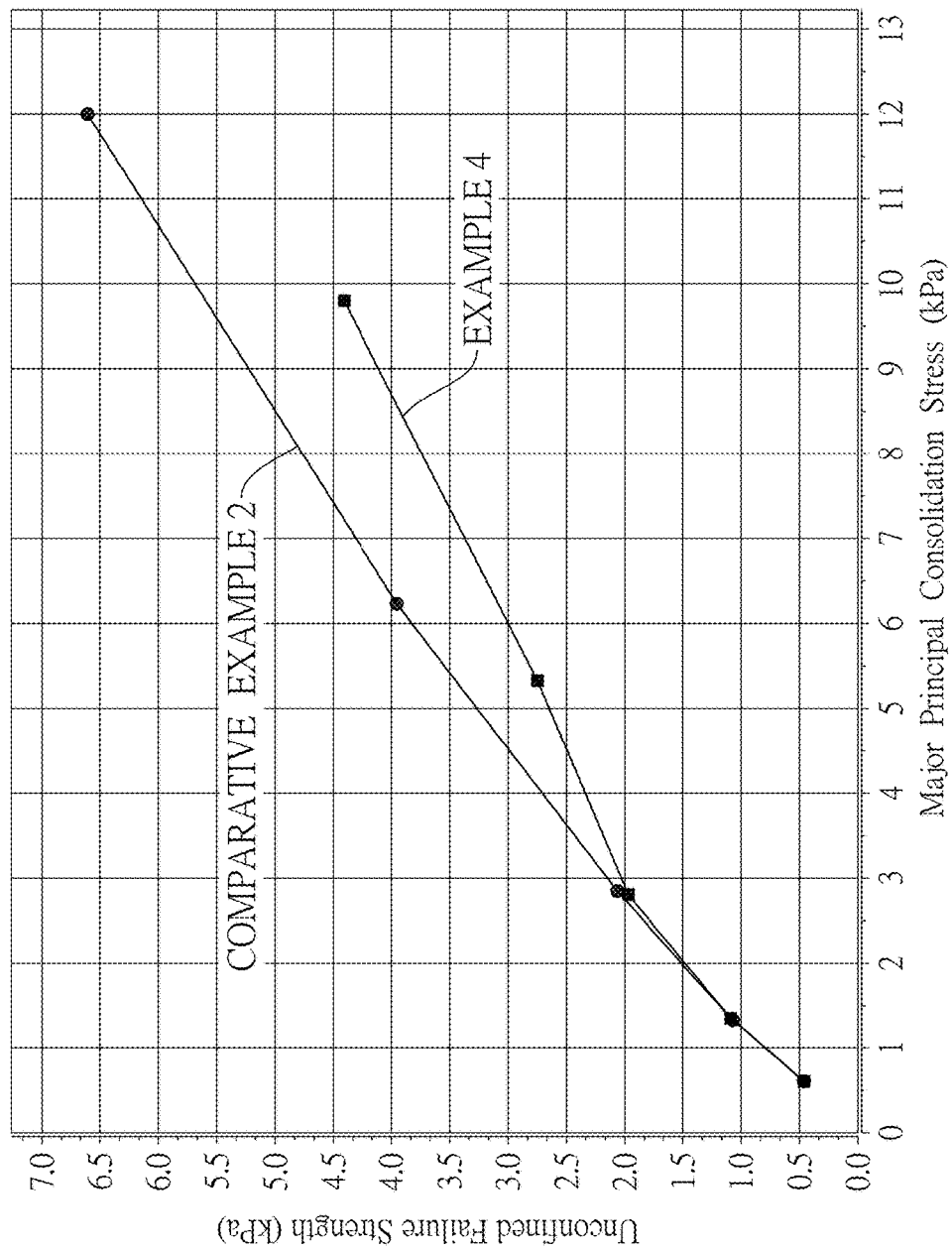
FIG. 7 shows a powder flow function graph of the powdery diacetal clarifying agents of Example 4 in accordance with the present invention and Comparative Example 2.

In the instant test example, 100 grams of each of the powdery diacetal clarifying agents of Example 4 and Comparative Example 2 was ground with RT-25 airflow-type ultrafine powder and high-speed grinder machine, and then installed in the standard plate and pressed with the powder flow tester to analyze the consolidation stress and the unconfined failure strength as shown in FIG. 7. With reference to FIG. 7, the slope of the powdery diacetal clarifying agent of Example 4 was apparently less than that of Comparative Example 2.

From foresaid tests, the inorganic silicon-containing compound was proved significantly useful to improve the flowability of the powdery diacetal clarifying agent.

Test Example 5: Properties of Plastic Article

In the instant test example, the powdery diacetal clarifying agents of Example 4 and Comparative Example 2 were used to prepare eight different polyolefin articles, each a 1.5 mm-thick plaque, for measurement. Each of the plaques of Samples 1 to 8 was prepared by the following steps.

(a) The plastic raw material and the polymers were mixed according to the amount as listed in Table 4, stirred, and granulated with an extruder under six heating zones at 180° C., 190° C., 215° C., 215° C., 215° C., 190° C. and a rotation of 40 revolutions per minute (rpm). The unit of the amount as listed in Table 4 was parts per hundred parts of resin (phr).

(b) The mixture was loaded into an injection machine (YC V-90 from Year-Chance Machinery Co., Ltd.) having five heating zones at 180° C., 195° C., 210° C., 220° C., 220° C. and a screw with a length/diameter ratio (L/D) of 22/1.

(c) The granulated resin composition was then injected into a mold with a dimension of 70 mm*50 mm*1.5 mm at 30° C. to obtain the plaque for measurement.

TABLE 4 the amount of the polyolefin and powdery diacetal clarifying agents of Example 4 and Comparative Example 2 (unit: phr).

| | Engage 8480 | Tairipro T3002 | Moplen RP242G | Borealis RB307MO | Titanpro SM198 | Comparative Example 2 | Example 4 |
|---|---|---|---|---|---|---|---|
| Sample 1 | 5 | 100 | — | — | — | 0.237 | — |
| Sample 2 | 5 | 100 | — | — | — | — | 0.237 |
| Sample 3 | 5 | — | 100 | — | — | 0.237 | — |
| Sample 4 | 5 | — | 100 | — | — | — | 0.237 |
| Sample 5 | 5 | — | — | 100 | — | 0.237 | — |
| Sample 6 | 5 | — | — | 100 | — | — | 0.237 |
| Sample 7 | 5 | — | — | — | 100 | 0.237 | — |
| Sample 8 | 5 | — | — | — | 100 | — | 0.237 |

The properties of the polyolefin articles were measured by the following instruments and methods.

1. Yellow index of the plaque after thermal aging was measured with HunterLab ColorFlex® EZ color meter.
2. Haze of the plaque was measured with BYK Gardner XL-211 hazemeter according to ASTM Standard Test Method D1003-61.
3. Crystallization temperature of the plaque was measured with a differential scanning calorimeter thermal analyzer.
4. Appearances of Samples 1 to 8 were evaluated by three skilled persons. The results were obtained from the total score evaluated by the three skilled persons. "1" indicated the plaque appeared yellow with low transparency. "2" indicated the plaque appeared transparent but yellow. "3" indicated the plaque appeared transparent and slightly yellow. "4" indicated the plaque appeared colorless but not quite transparent. "5" indicated the plaque appeared colorless and pretty transparent. The higher total score represented the plaque had a better appearance. The results were listed in Table 5.

TABLE 5 the total score of the appearance, YI, haze, and crystallization temperature of Samples 1 to 8.

| | Total score of appearance | YI | Haze value | Crystallization temperature |
|---|---|---|---|---|
| Sample 1 | 13 | 2.28 | 29.5 | 119.4° C. |
| Sample 2 | 15 | 1.44 | 29.4 | 119.4° C. |
| Sample 3 | 13 | 2.18 | 30.8 | 119.7° C. |
| Sample 4 | 15 | 1.71 | 31.8 | 120.2° C. |
| Sample 5 | 13 | 2.22 | 26.2 | 116.5° C. |
| Sample 6 | 15 | 1.81 | 26.2 | 116.5° C. |
| Sample 7 | 11 | −1.09 | 53.2 | 113.2° C. |
| Sample 8 | 12 | −1.46 | 53.2 | 112.8° C. |

According to the results of Table 5, the haze values and crystallization temperatures of Samples 2, 4, 6, and 8 were respectively close to those of Samples 1, 3, 5, and 7. Comparing the plaques prepared from Example 4 (Samples 2, 4, and 6) with those prepared from Comparative Example (Samples 1, 3, and 5), YI of Sample 2 was less than that of Sample 1, YI of Sample 4 was less than that of Sample 3, and YI of Sample 6 was less than that of Sample 5. Comparing the plaques prepared from Example 4 (Samples 2, 4, and 6) with those prepared from Comparative Example (Samples 1, 3, and 5), the total scores of Samples 2, 4, 6, and 8 were respectively higher than those of Samples 1, 3, 5, and 7. The results demonstrated that the powdery diacetal clarifying agent can allow the plastic articles made therefrom good color and thermal stabilities.

Test Example 6: Properties of Plastic Article

In the instant test example, each of the powdery diacetal clarifying agents of Examples 1, 4, and 6 to 8 and Comparative Examples 1 to 3, commercial products Geniset® DXR and LM30 was mixed with polypropylene random polymer (ST611) and other additives to prepare polyolefin articles of Samples 10 to 19, each a 1.5 mm-thick plaque.

As shown in Table 6, the powdery diacetal clarifying agents obtained by Examples 1, 4, and 6 to 8, Comparative Examples 1 to 3, and commercial products Geniset® DXR or LM30 were mixed with polypropylene random polymer (ST611), primary and secondary antioxidants and acid scavenger to form the polypropylene compositions or the preparation of polypropylene articles of Samples 10 to 19. Besides, a polypropylene composition without any powdery diacetal clarifying agent or commercial diacetal was also prepared as the control sample, and named as Sample 9.

TABLE 6 the reagents and their amount for preparation
of the polypropylene composition.

| Reagent | Amount (phr) |
| --- | --- |
| Polypropylene (ST611) | 100 phr |
| Primary Antioxidant (K-NOX 1010) | 0.06 phr |
| Secondary Antioxidant (K-NOX 168) | 0.12 phr |
| Acid Scavenger (Calcium Stearate) | 0.08 phr |
| Powdery diacetal clarifying agent | 0.22 phr |

Each of the polypropylene compositions was loaded into an injection machine (YC V-90 from Year-Chance Machinery Co., Ltd.) having five heating zones at 180° C., 195° C., 210° C., 225° C., 230° C. and a screw with a length/diameter ratio (L/D) of 22/1. The granulated polypropylene composition was then injected into a mold with a dimension of 50 mm*50 mm*1 mm at 30° C. to obtain the Samples 9 to 19.

Upon extruding the polypropylene composition out of the die, the releasing smell was evaluated and rated by three skilled persons. "0" represented that no odor difference between the odors released from the polypropylene composition and the control sample. "1" represented a very slight odor difference between the polypropylene composition and the control sample (Sample 9). "2" represented a slight odor difference between the polypropylene composition and the control sample. "3" represented a sensible odor difference between the polypropylene composition and the control sample. "4" represented that an obvious odor released by the polypropylene composition. "5" represented that a pungent odor released by the polypropylene composition. The total scores evaluated by the three skilled persons were listed in Table 7, the lower total score representing the plaque had a better smell, i.e., releasing no stinking odor.

For the evaluation of white spots, 10 pieces of each plaque were collected when extruded out of the die, and the apparent visible white spots were counted by three persons and summed up for evaluation. "0" represented that the plaque did not show any white spot. "1" represented that the plaque had 1 to 3 white spots in total. "2" represented that the plaque had 4 to 10 white spots in total. "3" represented that the plaque had 11 to 20 white spots in total. "4" represented that the plaque had 21 to 50 white spots in total. "5" represented that the plaque had more than 50 white spots in total. The fewer numbers of the white spots indicated that the powdery diacetal clarifying agent was formed in a more uniform distribution without aggregation. The results were listed in Table 7.

TABLE 7 the source of the powdery diacetal clarifying agent, abbreviated as source of diacetal, of Samples 9 to 19 and the haze value, crystallization temperature (Tc, unit: ° C.), odor evaluation, white spot evaluation, and yellow index of Samples 9 to 19

| | Source of diacetal | Haze value | Tc | Odor Evaluation | White Spot Evaluation | YI |
| --- | --- | --- | --- | --- | --- | --- |
| Sample 9 | Without diacetal | 44.0 | 104.5 | 0 | 0 | 1.19 |
| Sample 10 | Example 1 | 15.2 | 120.3 | 5 | 0 | 1.17 |
| Sample 11 | Example 4 | 10.9 | 121.9 | 2 | 0 | 0.65 |
| Sample 12 | Example 6 | 11.7 | 121.6 | 2 | 0 | 0.75 |
| Sample 13 | Example 7 | 12.2 | 121.1 | 3 | 0 | 0.95 |
| Sample 14 | Example 8 | 20.0 | 120.1 | 3 | 0 | −0.55 |
| Sample 15 | Comparative Example 1 | 14.2 | 116.4 | 7 | 0 | 2.33 |
| Sample 16 | Comparative Example 2 | 12.4 | 122.1 | 4 | 2 | 1.87 |
| Sample 17 | Comparative Example 3 | 11.5 | 119.1 | 6 | 1 | 1.95 |
| Sample 18 | Geniset ® DXR | 11.5 | 121.8 | 4 | 0 | 1.13 |
| Sample 19 | LM30 | 12.6 | 118.7 | 6 | 1 | 1.76 |

As shown in Table 7, the total scores of odor evaluation of Samples 11 to 14 were lower than those of Sample 15 to 19, and the total score of odor evaluation of Sample 10 was also lower than that of Sample 15. All plaques of Samples 10 to 14 did not show any white spots; however, the plaques of Samples 16, 17, and 19 showed at least one white spot. Besides, the YI of Sample 10 was closer to 0 than those of Samples 9 and 15, the YIs of Samples 11 to 14 were closer to 0 than those of Samples 15 to 19. It demonstrated that the powdery diacetal clarifying agent comprising the inorganic silicon-containing compound is useful to prevent the plastic articles made therefrom releasing stinking odor, showing white spots, and yellowing, and thus allows the plastic articles to have improved appearance and property.

In conclusion, the powdery diacetal clarifying agent in accordance with the present invention is highly pure and substantially free of impurities and volatile substances. Such a powdery diacetal clarifying agent has an excellent flowability and avoids being suspended in the air. In addition, the powdery diacetal clarifying agent does not release intolerable odor during the plastic processing, and prevents the final plastic article from yellowing under high temperature, typically a temperature higher than 190° C. Accordingly, the powdery diacetal clarifying agent in accordance with the present invention can guarantee the final plastic article's flowability, safety, color and thermal stabilities, thereby being widely applicable.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A powdery diacetal clarifying agent, comprising:
a diacetal compound selected from the group consisting of compounds represented by formulae (I) to (V):

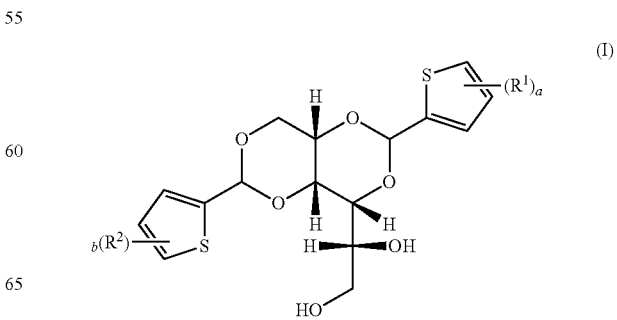

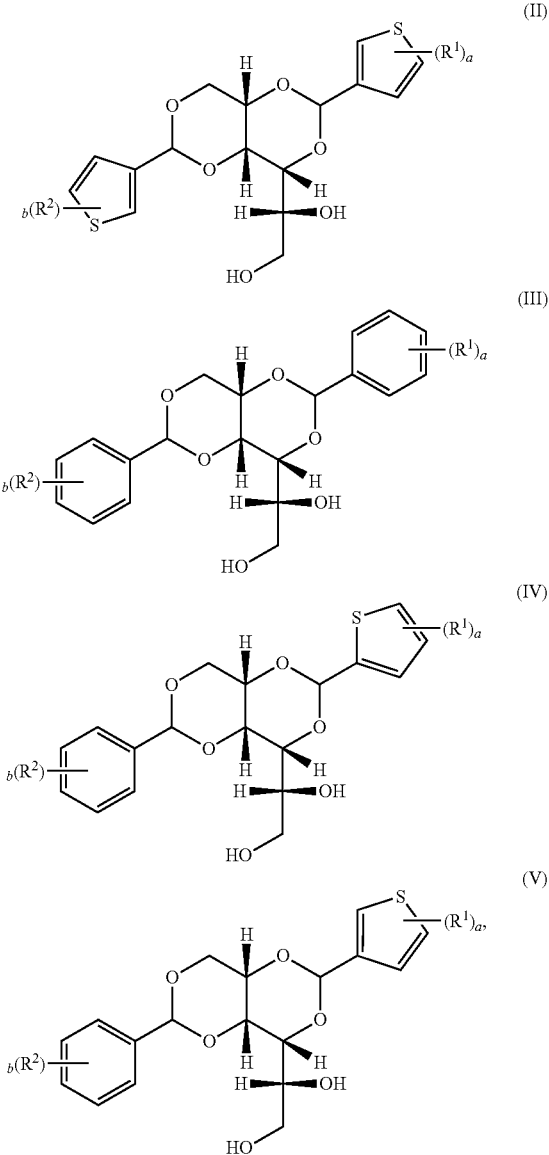

wherein R¹ and R² are each independently selected from the group consisting of hydrogen, an alkyl group having 1 to 4 carbon atoms, an alkoxy group having 1 to 4 carbon atoms, an alkoxycarbonyl group having 1 to 4 carbon atoms, fluoro, chloro, and bromo; wherein a and b are each independently an integral from 0 to 3; and an inorganic silicon-containing compound having a pH value equal to or more than 6 and equal to or less than 12 and having a median particle size equal to or less than 15 micrometers, wherein the inorganic silicon-containing compound is selected from the group consisting of sodium potassium aluminosilicate, calcium silicate, sodium calcium aluminosilicate, sodium aluminosilicate, potassium magnesium aluminosilicate, hydrated aluminosilicate, lithium magnesium sodium oxide silicate, an exfoliated montmorillonite silica nanomaterial, and combinations thereof.

2. The powdery diacetal clarifying agent as claimed in claim 1, wherein an amount of the inorganic silicon-containing compound ranges from 0.02 wt % to 3.0 wt % based on a total amount of the powdery diacetal clarifying agent.

3. The powdery diacetal clarifying agent as claimed in claim 2, wherein the amount of the inorganic silicon-containing compound ranges from 0.2 wt % to 1.0 wt % based on the total amount of the powdery diacetal clarifying agent.

4. The powdery diacetal clarifying agent as claimed in claim 1, wherein the diacetal compound is selected from the group consisting of: 1,3:2,4-di(5-methyl-2-thenylidene)-D-sorbitol; 1,3:2,4-di(4-methyl-benzylidene)-D-sorbitol; 1,3:2,4-di(4-n-butyl-benzylidene)-D-sorbitol, and 1,3:2,4-di(3,4-dimethyl-benzylidene)-D-sorbitol.

5. The powdery diacetal clarifying agent as claimed in claim 1, wherein the pH value of the inorganic silicon-containing compound is equal to or more than 8 and equal to or less than 10, and the median particle size of the inorganic silicon-containing compound is equal to or less than 10 micrometers.

6. The powdery diacetal clarifying agent as claimed in claim 5, wherein the inorganic silicon-containing compound is the sodium aluminosilicate, and the sodium aluminosilicate contains trisulfur radical anion.

7. The powdery diacetal clarifying agent as claimed in claim 1, wherein the inorganic silicon-containing compound is the exfoliated montmorillonite silica nanomaterial, the exfoliated montmorillonite silica nanomaterial has a median particle size less than 1 micrometer, and the pH value of the exfoliated montmorillonite silica nanomaterial is from pH 9 to pH 10.

8. The powdery diacetal clarifying agent as claimed in claim 1, wherein the inorganic silicon-containing compound is the lithium magnesium sodium oxide silicate, the lithium magnesium sodium oxide silicate has a median particle size less than 50 nanometers, and the pH value of the lithium magnesium sodium oxide silicate is from pH 9 to pH 10.

* * * * *